(12) United States Patent
Kanya et al.

(10) Patent No.: US 8,841,507 B2
(45) Date of Patent: Sep. 23, 2014

(54) ABSORBENT ARTICLE AND COMPONENTS THEREOF HAVING IMPROVED SOFTNESS SIGNALS, AND METHODS FOR MANUFACTURING

(75) Inventors: Kevin Ronald Kanya, Liberty Township, OH (US); W. Andrew Coslett, Drums, PA (US); John C. Parsons, Mountain Top, PA (US)

(73) Assignee: The Procter & Gamble Company, Cincinnati, OH (US)

( * ) Notice: Subject to any disclaimer, the term of this patent is extended or adjusted under 35 U.S.C. 154(b) by 318 days.

(21) Appl. No.: 13/213,198

(22) Filed: Aug. 19, 2011

(65) Prior Publication Data

US 2012/0179126 A1 Jul. 12, 2012

Related U.S. Application Data

(60) Provisional application No. 61/375,564, filed on Aug. 20, 2010.

(51) Int. Cl.
*A61F 13/15* (2006.01)
*A61F 13/514* (2006.01)

(52) U.S. Cl.
CPC ..... *A61F 13/51476* (2013.01); *A61F 13/51496* (2013.01); *A61F 13/5148* (2013.01)
USPC ......................................... 604/380

(58) Field of Classification Search
CPC ............ A61F 13/514; A61F 13/51476; A61F 13/51478; A61F 13/5148; A61F 2013/51078; A61F 2013/5108; A61F 2013/51083; A61F 2013/51085; A61F 2013/51088; A61F 2013/51095; A61F 2013/5149
See application file for complete search history.

(56) References Cited

U.S. PATENT DOCUMENTS 3,485,706 A 12/1969 Evans
3,989,867 A 11/1976 Sisson
(Continued)

FOREIGN PATENT DOCUMENTS

EP 0 834 938 B1 2/2002
JP 01-132862 A 5/1989
(Continued)

OTHER PUBLICATIONS

Insight Conference 2003 Presentation Highlights by Rieter Perfojet (51 pages).
(Continued)

*Primary Examiner* — Lynne Anderson
(74) *Attorney, Agent, or Firm* — William E. Gallagher

(57) ABSTRACT

An absorbent article having improved softness signals is disclosed. The article may include a topsheet or a backsheet including a nonwoven web. The web may have a basis weight of 30 gsm or less, may be formed of spunlaid fibers including polyolefin and up to 5 percent by weight $TiO_2$, and may be impressed with a pattern of bond impressions to a bond area percentage of at least 10 percent forming a pattern of bonded regions and raised regions. The web may have opacity of 42 or greater; have an average height difference between bonded regions and raised regions of at least 280 µm; be hydroengorged; and/or have a cross-direction tensile strength of 350 gf/cm. A nonwoven web manufactured to have a suitable combination of such features exhibits an enhanced appearance of softness, soft tactile feel and satisfactory mechanical attributes, while being relatively cost effective.

17 Claims, 7 Drawing Sheets

(56) References Cited

U.S. PATENT DOCUMENTS

| | | |
|---|---|---|
| 4,039,711 A | 8/1977 | Newman |
| 4,101,358 A | 7/1978 | Kim et al. |
| 4,127,637 A | 11/1978 | Pietreniak et al. |
| 4,333,979 A | 6/1982 | Sciaraffa et al. |
| 4,451,520 A | 5/1984 | Tecl et al. |
| 4,493,868 A | 1/1985 | Meitner |
| 4,725,473 A | 2/1988 | Van Gompel et al. |
| 4,735,849 A | 4/1988 | Murakami et al. |
| 4,774,110 A | 9/1988 | Murakami et al. |
| 4,808,467 A | 2/1989 | Suskind et al. |
| 4,810,556 A | 3/1989 | Kobayashi et al. |
| 4,921,643 A | 5/1990 | Walton et al. |
| 4,927,588 A | 5/1990 | Schultz |
| 4,940,464 A | 7/1990 | Van Gompel et al. |
| 4,950,531 A | 8/1990 | Radwanski et al. |
| 5,037,416 A | 8/1991 | Allen et al. |
| 5,092,861 A | 3/1992 | Nomura et al. |
| 5,098,764 A | 3/1992 | Bassett et al. |
| 5,136,761 A | 8/1992 | Sternlieb et al. |
| 5,151,230 A | 9/1992 | Damberg |
| 5,204,165 A | 4/1993 | Schortmann |
| 5,246,433 A | 9/1993 | Hasse et al. |
| 5,266,392 A | 11/1993 | Land et al. |
| 5,269,775 A | 12/1993 | Freeland et al. |
| 5,284,703 A | 2/1994 | Everhart et al. |
| 5,292,581 A | 3/1994 | Viazmensky et al. |
| 5,370,764 A | 12/1994 | Alikhan |
| 5,389,202 A | 2/1995 | Everhart et al. |
| 5,391,415 A | 2/1995 | Bair |
| 5,456,982 A | 10/1995 | Hansen et al. |
| 5,494,736 A | 2/1996 | Willey et al. |
| 5,533,991 A | 7/1996 | Kirby et al. |
| 5,536,555 A | 7/1996 | Zelazoski et al. |
| 5,554,145 A | 9/1996 | Roe et al. |
| 5,569,234 A | 10/1996 | Buell et al. |
| 5,571,096 A | 11/1996 | Dobrin et al. |
| 5,607,760 A | 3/1997 | Roe |
| 5,614,281 A | 3/1997 | Jackson et al. |
| 5,635,191 A | 6/1997 | Roe et al. |
| 5,643,588 A | 7/1997 | Roe et al. |
| 5,645,915 A | 7/1997 | Kranzler et al. |
| 5,645,916 A | 7/1997 | Oathout |
| 5,698,481 A | 12/1997 | VanHout et al. |
| 5,759,926 A | 6/1998 | Pike et al. |
| 5,843,057 A | 12/1998 | Mccormack |
| 5,897,545 A | 4/1999 | Kline et al. |
| 5,935,880 A | 8/1999 | Wang et al. |
| 5,938,648 A * | 8/1999 | LaVon et al. .................. 604/358 |
| 5,957,908 A | 9/1999 | Kline et al. |
| 5,961,505 A | 10/1999 | Coe et al. |
| 5,981,410 A | 11/1999 | Hansen et al. |
| 6,004,306 A | 12/1999 | Robles et al. |
| 6,093,665 A | 7/2000 | Sayovitz et al. |
| 6,110,848 A | 8/2000 | Bouchette |
| 6,120,487 A | 9/2000 | Ashton |
| 6,120,489 A | 9/2000 | Johnson et al. |
| 6,156,024 A | 12/2000 | Schulte et al. |
| 6,162,961 A | 12/2000 | Tanner et al. |
| 6,177,370 B1 | 1/2001 | Skoog et al. |
| 6,200,669 B1 | 3/2001 | Marmon et al. |
| 6,264,872 B1 | 7/2001 | Majors et al. |
| 6,277,104 B1 | 8/2001 | Lasko et al. |
| 6,321,425 B1 | 11/2001 | Putnam et al. |
| 6,348,253 B1 | 2/2002 | Daley et al. |
| 6,419,865 B1 | 7/2002 | Gryskiewicz et al. |
| 6,430,788 B1 | 8/2002 | Putnam et al. |
| 6,468,931 B1 | 10/2002 | Reeder et al. |
| 6,479,154 B1 | 11/2002 | Walton et al. |
| 6,491,777 B1 | 12/2002 | Bevins et al. |
| 6,537,644 B1 | 3/2003 | Kauschke et al. |
| 6,599,612 B1 | 7/2003 | Gray |
| 6,610,383 B1 | 8/2003 | Morman et al. |
| 6,610,390 B1 | 8/2003 | Kauschke et al. |
| 6,613,028 B1 | 9/2003 | Daley et al. |
| 6,632,385 B2 | 10/2003 | Kauschke et al. |
| 6,632,504 B1 | 10/2003 | Gillespie et al. |
| 6,645,569 B2 | 11/2003 | Cramer et al. |
| 6,735,833 B2 | 5/2004 | Putnam et al. |
| 6,743,321 B2 | 6/2004 | Guralski et al. |
| 6,780,372 B2 | 8/2004 | Gray |
| 6,794,557 B1 | 9/2004 | Klemp et al. |
| 6,803,103 B2 | 10/2004 | Kauschke et al. |
| 6,836,938 B2 | 1/2005 | Fleissner |
| 6,851,164 B2 | 2/2005 | Andersen |
| 6,861,571 B1 | 3/2005 | Roe et al. |
| 6,863,933 B2 | 3/2005 | Cramer et al. |
| 6,903,034 B1 | 6/2005 | Putnam et al. |
| 7,005,557 B2 | 2/2006 | Klofta et al. |
| 7,056,404 B2 | 6/2006 | McFall et al. |
| 7,080,584 B2 | 7/2006 | Boscolo |
| 7,091,140 B1 | 8/2006 | Ferencz et al. |
| 7,112,621 B2 | 9/2006 | Rohrbaugh et al. |
| 7,452,832 B2 | 11/2008 | Bansal et al. |
| 7,553,532 B2 | 6/2009 | Turner et al. |
| 7,670,971 B2 | 3/2010 | Brennan |
| 7,750,203 B2 | 7/2010 | Becker et al. |
| 7,851,047 B2 | 12/2010 | Sato et al. |
| 2002/0077618 A1 | 6/2002 | Molas |
| 2002/0104203 A1 | 8/2002 | Greenway |
| 2002/0143304 A1 | 10/2002 | Elder et al. |
| 2002/0144384 A1 | 10/2002 | Maugans |
| 2003/0106560 A1 | 6/2003 | Griesbach et al. |
| 2003/0118776 A1 | 6/2003 | Anderson et al. |
| 2003/0119403 A1 | 6/2003 | Willis et al. |
| 2003/0125695 A1 | 7/2003 | Dorschner |
| 2003/0135191 A1 | 7/2003 | Price et al. |
| 2003/0148684 A1 | 8/2003 | Cramer et al. |
| 2003/0203698 A1 | 10/2003 | Gillespie et al. |
| 2003/0233082 A1 | 12/2003 | Kline et al. |
| 2004/0010894 A1 | 1/2004 | Goldwasser et al. |
| 2004/0067709 A1 | 4/2004 | Kishine et al. |
| 2004/0122398 A1 * | 6/2004 | Schnabel et al. ......... 604/385.01 |
| 2004/0175343 A1 | 9/2004 | Osborne et al. |
| 2004/0198124 A1 | 10/2004 | Polanco et al. |
| 2004/0201125 A1 | 10/2004 | Allen et al. |
| 2004/0203309 A1 | 10/2004 | Allen et al. |
| 2005/0008839 A1 | 1/2005 | Cramer et al. |
| 2005/0077012 A1 | 4/2005 | Vuillaume |
| 2005/0136224 A1 | 6/2005 | Nickel et al. |
| 2005/0215156 A1 | 9/2005 | Ferencz et al. |
| 2008/0294140 A1 | 11/2008 | Ecker et al. |
| 2008/0306463 A1 | 12/2008 | Dent et al. |
| 2008/0312617 A1 | 12/2008 | Hundorf et al. |
| 2009/0022956 A1 * | 1/2009 | Hisamoto ..................... 428/156 |
| 2009/0118689 A1 | 5/2009 | Lawson et al. |
| 2010/0159774 A1 | 6/2010 | Chambers et al. |
| 2010/0159775 A1 | 6/2010 | Chambers et al. |
| 2012/0041410 A1 * | 2/2012 | Ueda et al. ............... 604/385.25 |

FOREIGN PATENT DOCUMENTS

| | | |
|---|---|---|
| JP | 07-236653 A | 9/1995 |
| JP | 07-276573 | 10/1995 |
| JP | 11-019015 A | 1/1999 |
| JP | 03-080859 | 10/2001 |
| JP | 2004-360130 | 12/2004 |
| WO | WO-95/16746 A1 | 6/1995 |
| WO | WO-99/16400 | 4/1999 |
| WO | WO-00/29658 A1 | 5/2000 |
| WO | WO-00/69481 A1 | 11/2000 |
| WO | WO 2007-114362 A1 | 10/2007 |

OTHER PUBLICATIONS

PCT International Search Report mailed Jan. 20, 2012 (21 pages).
U.S. Appl. No. 13/213,177, filed Aug. 19, 2011, Kanya et al.
U.S. Appl. No. 13/213,204, filed Aug. 19, 2011, Kanya et al.

* cited by examiner

ABSORBENT ARTICLE AND COMPONENTS THEREOF HAVING IMPROVED SOFTNESS SIGNALS, AND METHODS FOR MANUFACTURING

CROSS REFERENCE TO RELATED APPLICATION

This application claims the benefit of U.S. Provisional Application No. 61/375,564, filed Aug. 20, 2010, the substance of which is incorporated herein by reference.

BACKGROUND OF THE INVENTION

The business of manufacturing and marketing disposable absorbent articles for personal care or hygiene (such as disposable diapers, training pants, adult incontinence undergarments, feminine hygiene products, breast pads, care mats, bibs, wound dressing products, and the like) is relatively capital intensive and highly competitive. To maintain or grow their market share and thereby maintain a successful business, manufacturers of such articles must continually strive to enhance their products in ways that serve to differentiate them from those of their competitors, while at the same time controlling costs so as to enable competitive pricing and the offering to the market of an attractive value-to-price proposition.

One way in which some manufacturers may seek to enhance such products is through enhancements to softness. Parents and caregivers naturally seek to provide as much comfort as they can for their babies, and utilizing products such as disposable diapers that they perceive as relatively soft provides reassurance that they are doing what they can to provide comfort in that context. With respect to other types of disposable absorbent articles that are designed to be applied and/or worn close the skin, an appearance of softness can reassure the wearer or caregiver that the article will be comfortable.

Thus, manufacturers may devote efforts toward enhancing the softness of the various materials used to make such products, such as various web materials, including nonwoven web materials formed from polymer fibers, and laminates thereof, forming the products. Such laminates may include, for example, laminates of polymer films and nonwoven web materials forming the backsheet components of the products.

It is believed that humans' perceptions of softness of a nonwoven web material can be affected by tactile signals, auditory signals and visual signals.

Tactile softness signals may be affected by a variety of the material's features and properties that have effect on its tactile feel, including but not limited to loft, fiber thickness and density, basis weight, microscopic pliability and flexibility of individual fibers, macroscopic pliability and flexibility of the nonwoven web as formed by the fibers, surface friction characteristics, number of loose fibers or free fiber ends, and other features.

Perceptions of softness also may be affected by auditory signals, e.g., whether and to what extent the material makes audible rustling, crinkling or other noises when touched or manipulated.

It is believed that perceptions of softness of a material also may be affected by visual signals, i.e., its visual appearance. It is believed that, if a nonwoven material looks relatively soft to a person, it is much more likely that the person will perceive it as having relative tactile softness as well. Visual impressions of softness may be affected by a variety of features and properties, including but not limited to color, opacity, light reflectivity, refractivity or absorption, apparent thickness/caliper, fiber size and density, and macroscopic physical surface features.

As a result of the complexity of the mix of the above-described characteristics, to the extent softness is considered an attribute of a nonwoven web material, it may elude precise measurement or quantification. Although several methods for measuring and evaluating material features that are believed to affect softness signals have been developed, there are no standard, universally accepted units or methods of measurement for softness. It is a subjective, relative concept, difficult to characterize in an objective way. Because softness is difficult to characterize, it can also be difficult to affect in a predictable way, through changes or adjustments to specifications in materials or manufacturing processes.

Complicating efforts to define and enhance softness is the fact that differing individuals will have differing individual physiological and experiential frames of reference and perceptions concerning what material features and properties will cause them to perceive softness to a lesser or greater extent in a material, and relative other materials.

Various efforts have been made to provide or alter features of nonwoven web materials with the objective of enhancing consumer perceptions of softness. These efforts have included selection and/or manipulation of fiber chemistry, basis weight, loft, fiber density, configuration and size, tinting and/or opacifying, embossing or bonding in various patterns, etc.

For example, one approach to enhancing perceived softness of a nonwoven web has involved simply increasing the basis weight of the web, otherwise manufactured through a spunlaid/spunbond process that includes formation of a batt of loose spun fibers and then consolidating by calender-bonding in a pattern. All other variables remaining constant, increasing the basis weight of such a web will have the effect of increasing the number of fibers per unit surface area, and correspondingly, increasing apparent thickness, fiber density and/or loft. This approach might be deemed effective if the only objective is increasing depth and/or loft signals affecting perceptions of softness, i.e., simply increasing the basis weight of a spunbond nonwoven is one way to increase its depth or loft. However, among the costs involved in producing nonwoven web material formed of polymer fibers is the cost of the polymer resin(s) from which the fibers are spun. Higher basis weight nonwovens require more resin to produce, and therefore, cost more per unit. Thus, attempting to enhance perceived softness by increasing nonwoven basis weight is incompatible with the ever-present objective of controlling or reducing costs.

Another approach has involved forming a nonwoven web of "bicomponent" polymer fibers, by spinning such fibers, laying them to form a batt and then consolidating them by calender-bonding with a pattern, to provide visual effects. Such bicomponent polymer fibers are formed by spinnerets that have two side-by-side sections, that express a first polymer on one side and a second polymer on the other, to form a fiber having a cross section of the first polymer on one side and the second polymer on the other (hence the term "bicomponent"). The respective polymers may be selected so as to have differing melting temperatures and/or expansion-contraction rates. These differing attributes of the two polymers cause the bicomponent fiber products to curl in the spinning process, as they exit the spinnerets and cool. The resulting curled fibers then may be laid down in a batt and calender-bonded in a pattern. It is thought that the curl in the fibers adds loft and fluff to the web, enhancing softness visual and tactile softness signals.

In another approach relating to a backsheet laminate of a film and a non-woven web, prior to lamination with a non-woven web the film is printed with a subtle pattern which, following lamination with the nonwoven web, is visible therethrough and simulates actual shading that would occur on the nonwoven web surface under various lighting conditions, as if it actually bore a pattern of three-dimensional surface features. The desired effect is to enhance visual softness signals.

Still another approach has involved adding and blending in a white tinting/opacifying agent (for example, titanium dioxide) to the polymer used to form a base layer of fibers forming the nonwoven web, forming the base layer, then forming additional layers by laying down fibers formed of untinted polymer over the base layer, to form a multi-layer batt. Following formation of the multi-layer batt, it is calender-bonded in a pattern, and then subjected to a hydroenhancing or hydroengorgement process to fluff the fibers and increase caliper and loft. It was thought that the presence of untinted, relatively translucent, shiny fibers laid over and interspersed with the base layer of tinted fibers, together with the hydroenhancing/hydroengorgement process, creates visual effects tending to enhance the perception of loft and/or depth. It is also believed that the hydroenhancing/hydroengorgement process actually increases loft and/or caliper, enhancing visual and tactile softness signals.

Still another approach has related to the manner in which products are packaged. Typically, absorbent products such as diapers and feminine hygiene products are packaged in stacked groups. During packaging, the stacks are usually compressed along a direction approximately orthogonal to the major portions of the surfaces formed by nonwovens, such that the caliper and loft of the nonwovens tends to be reduced by compression when packaged. The effect of the compression may subsist after removal of the product from a package, adversely affecting softness signals. Thus, it was thought that reducing the amount of compression in packaging would help to preserve caliper and loft of the nonwovens, and thus preserve the appearance of softness. It will be appreciated, however, that reducing the compression in packaging necessarily has the effect of either reducing the number of products per package, or increasing package size—both of which increase the per-product cost.

The approaches described above have had varying degrees of success, but have left room for improvement in enhancing visual and/or tactile softness signals. Additionally, many current methods for enhancing softness signals in a nonwoven web have the undesirable effect of decreasing desirable mechanical properties such as tensile strength. Generally, it is believed that, for any particular nonwoven web material, processing steps that increase softness signals undesirably decrease strength.

DETAILED DESCRIPTION OF THE INVENTION

Definitions

Figure 1A:
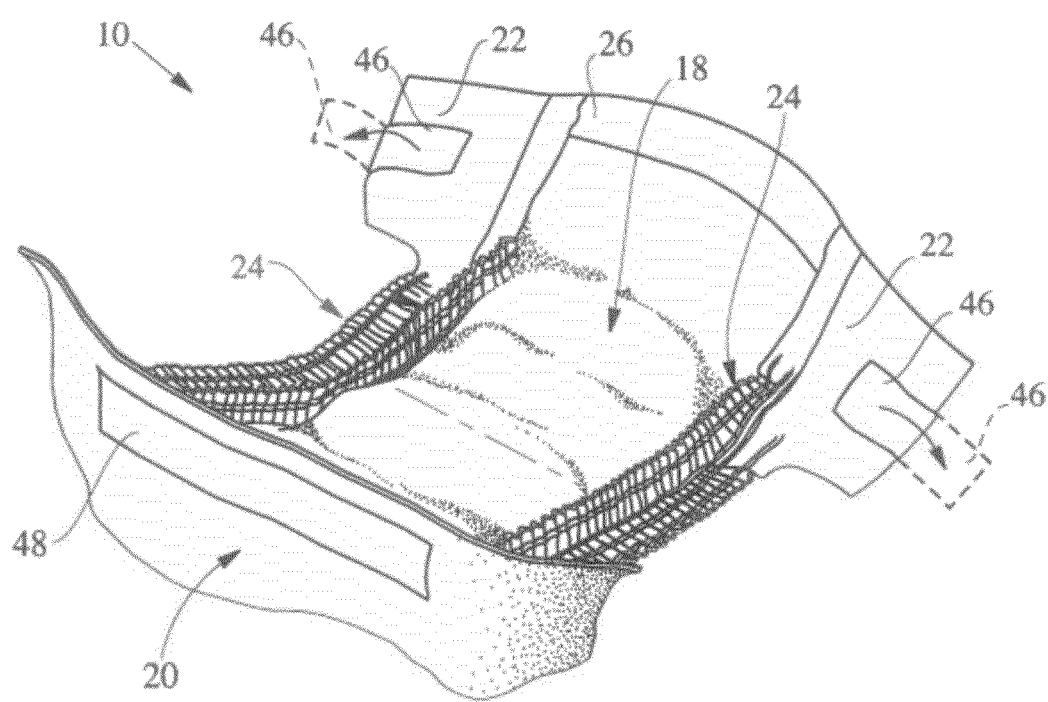
FIG. 1A is a perspective view of a disposable diaper shown laid out horizontally in a relaxed state, wearer-facing surfaces up.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments and pads, feminine hygiene products, breast pads, care mats, bibs, wound dressing products, and the like. As used herein, the term "exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article. The absorbent core may also include a cover layer or envelope. The cover layer or envelope may comprise a nonwoven. In some examples, the absorbent core may include one or more substrates, an absorbent polymer material, and a thermoplastic adhesive material/composition adhering and immobilizing the absorbent polymer material to a substrate, and optionally a cover layer or envelope.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein the first substrate and second substrate are separated by a multiplicity of superabsorbent particles. There may be some extraneous superabsorbent particles outside of this area between the first substrate 64 and second substrate.

"Airfelt" is used herein to refer to comminuted wood pulp, which is a form of cellulosic fiber.

"Average Measured Height" is an average difference in z-direction height between raised, unbonded areas, and bond impressions, of a nonwoven web component of a laminate of a polymeric film and a nonwoven web, measured and calculated according to the Average Measured Height Method set forth herein.

"Bicomponent" refers to fiber having a cross-section comprising two discrete polymer components, two discrete blends of polymer components, or one discrete polymer component and one discrete blend of polymer components. "Bicomponent fiber" is encompassed within the term "Multicomponent fiber." A Bicomponent fiber may have an overall cross section divided into two or more subsections of the differing components of any shape or arrangement, including, for example, coaxial subsections, core-and-sheath subsections, side-by-side subsections, radial subsections, etc.

"Bond Area Percentage" on a nonwoven web is a ratio of area occupied by bond impressions, to the total surface area of the web, expressed as a percentage, and measured according to the Bond Area Percentage method set forth herein.

"Bond Length Ratio" is a value expressed as percentage, and is the ratio of the sum of lengths of a repeating series of bond impressions on a nonwoven web along a theoretical line segment through and connecting the bond impressions in the series, and extending from a leading edge of the bond impression beginning the series, to a leading edge of the bond impression beginning the next adjacent repeating series, to the total length of the line segment, and is determined according to the Bond Path/Bond Length Ratio measurement method set forth herein. By way of non-limiting illustration FIG. 3B in which length $D_0$ is the length of a line segment and lengths $D_1$, $D_2$ and $D_3$ are lengths along the line segment of three bond impressions in a hypothetical repeating series of substantially identical bond impressions 100a as shown in FIG. 3B, a Bond Length Ratio may be calculated as $[(D_1+D_2+D_3)/D_0]\times 100\%$. It will be noted that if all bond impressions 100a as exemplified in FIG. 3B are identical in area, shape and spacing, any group of them in any number along a line segment will constitute a repeating series. However, bond impressions forming a path also may have differing areas, shapes and/or spacing, and it may be necessary to identify a repeating series of bond impressions of any other particular number in order to determine Bond Length Ratio.

"Bonding roller," "calender roller" and "roller" are used interchangeably.

"Cross direction"—with respect to a web material, refers to the direction along the web material substantially perpendicular to the direction of forward travel of the web material through the manufacturing line in which the web material is manufactured.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pant" which is defined below.

"Fiber" and "filament" are used interchangeably.

"Film"—means a skin-like or membrane-like layer of material formed of one or more polymers, which does not have a form consisting predominately of a web-like structure of consolidated polymer fibers and/or other fibers.

"Length" or a form thereof, with respect to a diaper or training pant, refers to a dimension measured along a direction perpendicular to the waist edges and/or parallel to the longitudinal axis.

"Machine direction"—with respect to a web material, refers to the direction along the web material substantially parallel to the direction of forward travel of the web material through the manufacturing line in which the web material is manufactured.

"Monocomponent" refers to fiber formed of a single polymer component or single blend of polymer components, as distinguished from Bicomponent or Multicomponent fiber.

"Multicomponent" refers to fiber having a cross-section comprising more than one discrete polymer component, more than one discrete blend of polymer components, or at least one discrete polymer component and at least one discrete blend of polymer components. "Multicomponent fiber" includes, but is not limited to, "Bicomponent fiber." A Multicomponent fiber may have an overall cross section divided into subsections of the differing components of any shape or arrangement, including, for example, coaxial subsections, core-and-sheath subsections, side-by-side subsections, radial subsections, etc.

A "nonwoven" is a manufactured sheet or web of directionally or randomly oriented fibers, consolidated and bonded together by friction, cohesion, adhesion or one or more patterns of bonds and bond impressions created through localized compression and/or application of heat or heating energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Opacity" is a numeric value relating to the ability of a web material to transmit light therethrough, measured according the Opacity Measurement Method set forth herein. "Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Tensile Strength" refers to the maximum tensile force (Peak Force) a material will sustain before tensile failure, as measured by the Tensile Strength Measurement Method set forth herein.

"Thickness" and "caliper" are used herein interchangeably.

"Total Stiffness" refers to the measured and calculated value relating to a material, according to the Stiffness measurement method set forth herein.

"Width" or a form thereof, with respect to a diaper or training pant, refers to a dimension measured along a direction parallel to the waist edges and/or perpendicular to the longitudinal axis.

"Z-direction," with respect to a web, means generally orthogonal or perpendicular to the plane approximated by the web in the machine and cross direction dimensions.

Examples of the present invention include disposable absorbent articles having improved softness attributes.

Figure 1B:
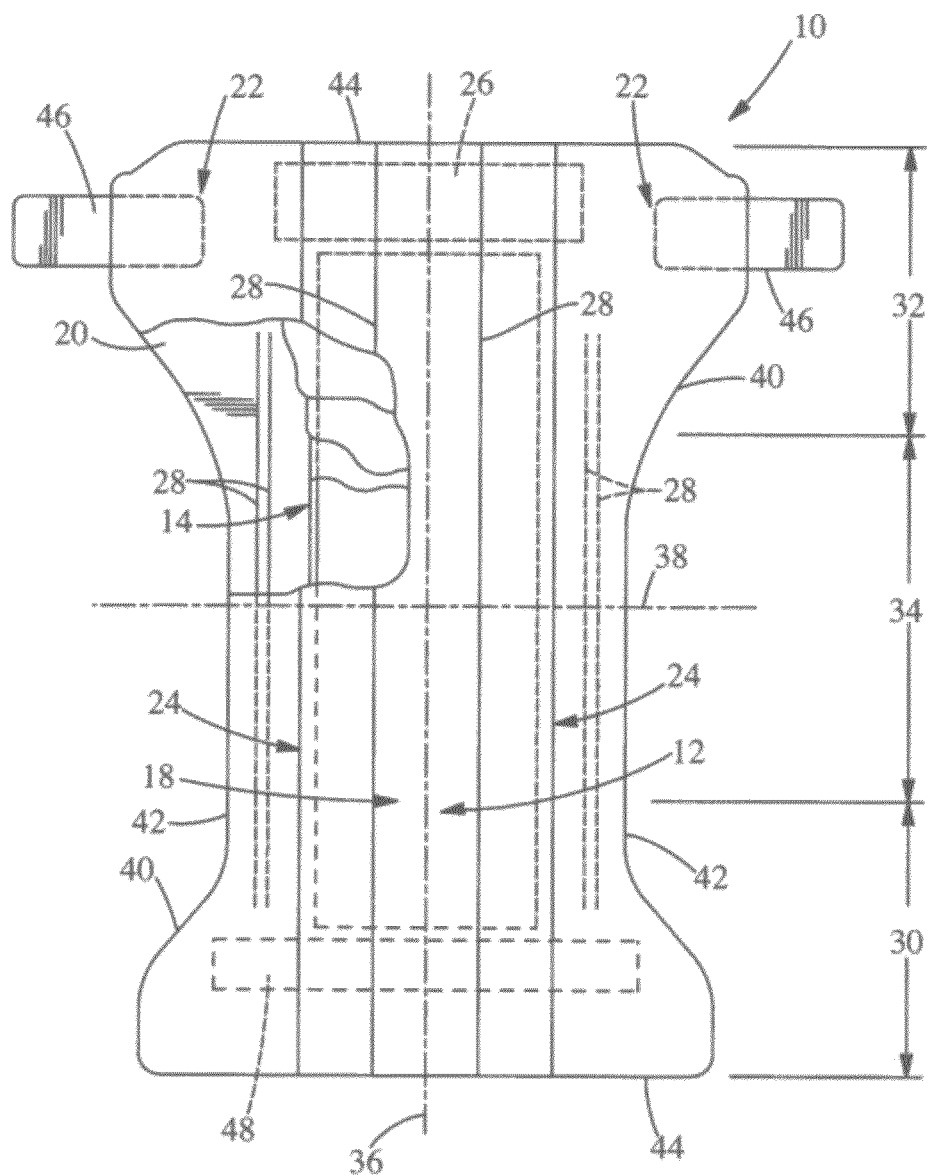
FIG. 1B is a plan view of a disposable diaper shown laid out horizontally in a stretched out, flattened state (stretched out against elastic contraction induced by the presence of elastic members), wearer-facing surfaces facing the viewer.
Figure 2A:
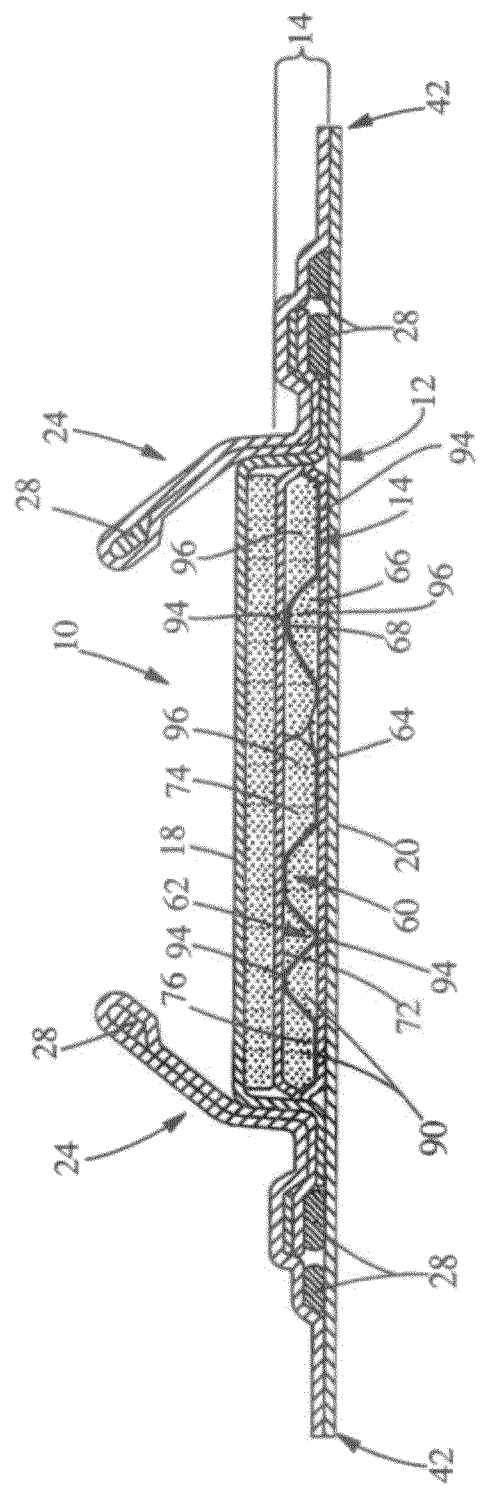
FIG. 2A is a cross section of the diaper depicted in FIGS. 1A and 1B, taken through line 2-2 in those figures.

FIG. 1A is a perspective view of a diaper 10 in a relaxed, laid-open position as it might appear opened and lying on a horizontal surface. FIG. 1B is a plan view of a diaper 10 shown in a flat-out, uncontracted state (i.e., without elastic induced contraction), shown with portions of the diaper 10 cut away to show underlying structure. The diaper 10 is depicted in FIG. 1B with its longitudinal axis 36 and its lateral axis 38. Portions of the diaper 10 that contact a wearer are shown oriented upwards in FIG. 1A, and are shown facing the viewer in FIG. 1B. FIG. 2A is a cross section of the diaper taken at line 2-2 in FIG. 1B.

The diaper 10 generally may comprise a chassis 12 and an absorbent core 14 disposed in the chassis. The chassis 12 may comprise the main body of the diaper 10.

The chassis 12 may include a topsheet 18, which may be liquid pervious, and a backsheet 20, which may be liquid impervious. The absorbent core 14 may be encased between the topsheet 18 and the backsheet 20. The chassis 12 may also include side panels 22, elasticized leg cuffs 24, and an elastic waist feature 26. The chassis 12 may also comprise a fastening system, which may include at least one fastening member 46 and at least one landing zone 48.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The crotch region 34 may include from 33.3% to 50% of the overall length of the diaper 10, and each of waist regions 30, 32 may correspondingly include from 25% to 33.3% of the overall length of the diaper 10.

The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 may also include such other features including front and rear ear panels, waist cap features, elastics and the like to provide better fit, containment and aesthetic characteristics. Such additional features are described in, e.g., U.S. Pats. Nos. 3,860,003 and 5,151,092.

In order to apply and keep diaper 10 in place about a wearer, the second waist region 32 may be attached by the fastening member 46 to the first waist region 30 to form leg opening(s) and an article waist. When fastened, the fastening system carries a tensile load around the article waist.

According to some examples, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, stretch laminates, activated stretch laminates, fiber reinforced plastics and the like, or combinations thereof. In some examples, the materials making up the fastening device may be flexible. In some examples, the fastening device may comprise cotton or cotton-like materials for additional softness or consumer perception of softness. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 may be fully or partially elasticized and/or may be foreshortened to create a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

Figure 2B:
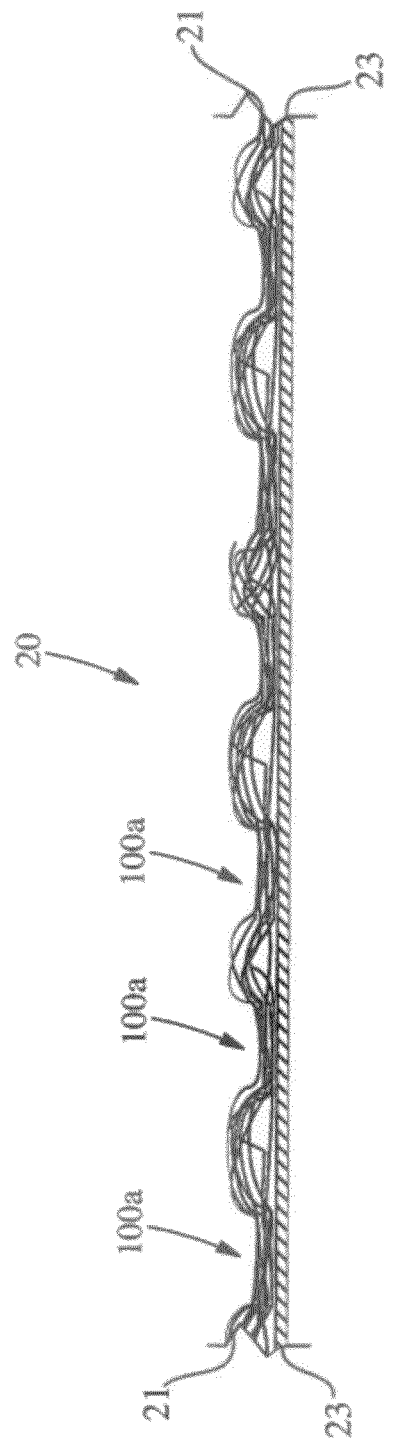
FIG. 2B is a schematic cross section of a portion of a laminate of a polymeric film and a nonwoven web, taken through a path of bond impressions.

The backsheet 20 may be joined with the topsheet 18. The backsheet 20 may serve prevent the exudates absorbed by the absorbent core 14 and contained within the diaper 10 from soiling other external articles that may contact the diaper 10, such as bed sheets and clothing. Referring to FIG. 2B, the backsheet 20 may be substantially impervious to liquids (e.g., urine) and comprise a laminate of a nonwoven 21 and a thin polymeric film 23 such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 20. Exemplary breathable materials may include materials such as woven webs, nonwoven webs, composite materials such as film-coated nonwoven webs, and microporous films such as manufactured by Mitsui Toatsu Co., of Japan under the designation ESPOIR and by EXXON Chemical Co., of Bay City, Tex., under the designation EXXAIRE. Suitable breathable composite materials comprising polymer blends are available from Clopay Corporation, Cincinnati, Ohio under the name HYTREL blend P1 8-3097. Other examples of such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

In some examples, the backsheet of the present invention may have a water vapor transmission rate (WVTR) of greater than about 2,000 g/24 h/m2, greater than about 3,000 g/24 h/m2, greater than about 5,000 g/24 h/m2, greater than about 6,000 g/24 h/m2, greater than about 7,000 g/24 h/m2, greater than about 8,000 g/24 h/m2, greater than about 9,000 g/24 h/m2, greater than about 10,000 g/24 h/m2, greater than about 11,000 g/24 h/m2, greater than about 12,000 g/24 h/m2, greater than about 15,000 g/24 h/m2, measured according to WSP 70.5 (08) at 37.8° C. and 60% Relative Humidity.

Suitable non-woven materials useful in the present invention include, but are not limited to SMS material, comprising a spunbonded, a melt-blown and a further spunbonded layer. In some examples, permanently hydrophilic non-wovens, and in particular, nonwovens with durably hydrophilic coatings may be desirable. Another suitable embodiment comprises a SMMS-structure. In some examples, the non-wovens may be porous.

In some examples, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to one example, a suitable nanoparticle coated non-woven is that disclosed in the co-pending patent application Ser. No. 10/758,066 entitled "Disposable absorbent article comprising a durable hydrophilic core wrap" by Ponomarenko and Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent application Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. In some examples, the nonwoven may comprise fibers having different degrees or types of curling, or both. For example, one embodiment may include a mixture of fibers having about 3 to about 5 curls per centimeter (cpc) or about 3.5 to about 4 cpc, and other fibers having about 1.5 to about 3.2 cpc or about 2 to about 2.8 cpc.

Different types of curls include, but are not limited to a 2D curl or "flat curl" and a 3D or spiral-curl. According to one example, the fibers may include bicomponent fibers, which are individual fibers each comprising different materials, usually a first and a second polymeric material. It is believed that the use of side-by-side bi-component fibers is beneficial for imparting a spiral curl to the fibers.

In order to enhance softness perceptions of the absorbent article, nonwovens forming the backsheet may be hydroenhanced or hydroengorged. Hydroenhanced/hydroengorged nonwovens are described in U.S. Pat. Nos. 6,632,385 and 6,803,103, and U.S. Pat. App. Pub. No. 2006/0057921.

A nonwoven may also be treated by a "selfing" mechanism. By "selfing" nonwovens, high densities of loops (>150 in 2) may be formed which protrude from the surface of the non-woven substrate. Since these loops act as small flexible brushes, they create an additional layer of springy loft, which may enhance softness. Nonwovens treated by a selfing mechanism are described in U.S. Pat. App. Pub. No. US 2004/0131820.

Nonwovens also may include a surface coating. In one example, the surface coating may include a fiber surface modifying agent, that reduces surface friction and enhances tactile lubricity. Preferred fiber surface modifying agents are described in U.S. Pat. Nos. 6,632,385 and 6,803,103; and U.S. Pat. App. Pub. No. 2006/0057921.

A surface coating also may inlcude a surfactant coating. One such surfactant coating is available from Schill & Silacher GmbH, Böblingen, Germany, under the Tradename Silastol PST.

Any of the nonwovens described herein may be used for the topsheet, backsheet, or any other portion of the absorbent article comprising a nonwoven. In order to achieve improved softness of the absorbent article, the nonwovens of the present invention may have a basis weight of greater than about 20 gsm, greater than about 22 gsm, greater than about 24 gsm, greater than about 26 gsm, greater than about 28 gsm, greater than about 30 gsm, greater than about 32 gsm.

The absorbent core generally may be disposed between the topsheet 18 and the backsheet 20. It may include one or more layers, such as a first absorbent layer 60 and a second absorbent layer 62.

The absorbent layers 60, 62 may include respective substrates 64, 72, an absorbent particulate polymer material 66, 74 disposed on substrates 64, 72, and a thermoplastic adhesive material 68, 76 disposed on and/or within the absorbent particulate polymer material 66, 74 and at least portions of the substrates 64, 72 as an adhesive for immobilizing the absorbent particulate polymer material 66, 74 on the substrates 64, 65.

The substrate 64 of the first absorbent layer 60 may be referred to as a dusting layer and has a first surface which faces the backsheet 20 and a second surface which faces the absorbent particulate polymer material 66. Likewise, the substrate 72 of the second absorbent layer 62 may be referred to as a core cover and has a first surface facing the topsheet 18 and a second surface facing the absorbent particulate polymer material 74.

The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

The substrates 64, 72 may be of one or more nonwoven materials, and may be liquid permeable.

As illustrated in FIG. 2A, the absorbent particulate polymer material 66, 74 may be deposited on the respective substrates 64, 72 in clusters 90 of particles to form a grid pattern comprising land areas 94 and junction areas 96 between the land areas 94. Land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern contain little or no absorbent particulate polymer material 66 and 74. The land areas 94 and junction areas 96 can have a variety of shapes including, but not limited to, circular, oval, square, rectangular, triangular, and the like. First and second layers 60, 62 may be combined to form the absorbent core 14. Preferred absorbent articles and cores are described in U.S. application Ser. No. 12/141,122; U.S. Pat. Apps. Pub. Nos. 2004/0167486 A1 and 2004/0162536; and PCT Pub. No. WO 2009/060384.

Signal ingredients may be incorporated into one or more components of the absorbent article. Signal ingredients may include, but are not limited to, vitamins A, E, D, and C, panthenol, niacin, omega 3 oils, cocoa butter, beeswax, cashmere, sweet almond oil, jojoba, oatmeal, aloe, cotton, honey, and silk. These signal ingredients may be added to an absorbent article for the purpose of signaling a benefit to the consumer. As an example, one or more of these signal ingredients may be added to a lotion that may be applied to an absorbent article component. The signal ingredient alone, or in a lotion, may be applied to the topsheet, backsheet, or any other component of the absorbent article. The lotion may comprise less than about 0.1% by weight, less than about 0.01% by weight, less than about 0.006% by weight, less than about 0.005% by weight, less than about 0.004% by weight, less than about 0.003% by weight, less than about 0.002% by weight, and less than about 0.001% by weight of the signal ingredient.

Additionally, a signal ingredient may, in combination with other absorbent article features, result in an unexpected synergy for communicating a benefit to the consumer. As an example, consumers may respond unexpectedly more favorably to an absorbent article that is thin and perceptibly soft in combination with a communication that lotion in the diaper comprises vitamin E than they would respond to either communication on its own.

An example of a diaper lotion comprising vitamin E as a signal ingredient may include the following formula: PET/StOH Mix (ratio=1.41) 94.0% to 99.8% (by weight) Aloe Extract 0.1% to 3.0% (by weight) Vitamin E 0.001% to 0.1% (by weight). Further, vitamin E may be used in its natural form or esters of natural vitamin E may be used (e.g., vitamin E acetate). U.S. App. Pub. Nos. 2002/0143304; 2004/0175343; 2003/0077307; U.S. Pat. Nos. 5,643,588; 5,635,191; 5,607,760; 6,861,571; and PCT Application Nos. WO 00/69481; and WO 98/24391 disclose various absorbent article lotions that signal ingredients may be added to.

Another way to achieve improved softness of the absorbent article may be through a lower in-bag compression. Lower compression rates result in a softer feeling absorbent article. Preferred in-bag compression percentages of the present invention are less than about 54%, less than about 52%, less than about 50%, less than about 49%, less than about 48%, less than about 47%, less than about 46%. For purposes herein, in-bag compression percentage is determined according to the In-Bag Compression Measurement Test set forth below.

Enhanced Nonwoven Webs Used for Topsheets and/or Backsheet Laminates

The foregoing description describes features of an absorbent article, any combination of which can be employed to enhance consumer perceptions of softness of the article. In addition, however, it is believed that manufacturing a nonwoven web, which may be used as a component of an absorbent article including, e.g., a topsheet 18 and/or backsheet 20 (see FIGS. 2A, 2B), according to the following description, provides for enhancement of softness signals of the component, and has synergistic effects with respect to enhancing perceptions of softness of the article as a whole. At the same time, counterintuitively, features described below enhance tensile strength of the nonwoven web, and consequently, of the topsheet, backsheet or other component formed of it. When attempting to improve softness signals, preserving or enhancing tensile strength of a nonwoven may be of particular interest in absorbent articles for at least two reasons. First, the nonwoven web may typically be required to sustain certain minimum tensile forces and undergo sufficiently low changes in dimension so as to be effectively processable in downstream manufacturing operations. Second, the nonwoven web typically may be a substantial contributor to structural integrity of a backsheet laminate in absorbent products such as disposable diapers, in which the backsheet may be required to sustain forces resulting from application/donning on a wearer (e.g., when a caregiver tugs on fastening members to apply a diaper), wearer movements, and bulk and weight and bulk contained and sustained by the backsheet when the diaper is loaded with the wearer's exudates.

As previously noted, a backsheet 20 may be formed of a laminate of a nonwoven and a thin polymeric film. In some examples, the polymeric film may have a thickness of about 0.012 mm (0.5 mil) to about 0.051 mm (2.0 mils). In order to achieve the desired overall visual appearance, the opacity and whiteness of the backsheet laminate may be enhanced by addition of, for example, calcium carbonate ($CaCO_3$) to the film during its formation. Inclusion of fine particles of $CaCO_3$ cause the formation of micropores about the particles upon stretching, or biaxial stretching in processing of the film, which serve to make the resulting film air- and vapor-permeable (thus, "breathable", reducing the likelihood of skin overhydration and thereby reducing the likelihood of conditions such as diaper rash). The $CaCO_3$ particles and the resulting micropores in the film also serve to enhance its opacity. Examples of suitable films include MICROPRO microporous films, and films designated BR137P and BR137U, available from Clopay Corporation, Mason, Ohio.

In some examples, the polymeric film may be formed of components, and as described, in U.S. application Pub. No. 2008/0306463, and may include some or all of the features and/or components described therein, that reduce the film's vulnerability to glue "burn-through."

The nonwoven web may be a hydroengorged spunbond nonwoven with a quilted bonding pattern and possessing two-sided properties due to a combination of materials and hydraulic treatment. The nonwoven may be formed to have an outer-facing side/surface having a pronounced quilted appearance and enhanced softness attributes, whereas the inner-facing side/surface many not necessarily require enhanced softness attributes.

The nonwoven web may be formed from one or more resins of polyolefins including but not limited to polypropylene (PP), polyethylene (PE), and polyethylene terephthalate (PET), and blends thereof. Resins including polypropylene may be particularly useful because of polypropylene's relatively low cost and surface friction properties of fibers formed from it (i.e., they have a relatively smooth, slippery tactile feel). Resins including polyethylene may also be desirable because of polyethylene's relative softness/pliability and even more smooth/slippery surface friction properties. Relative each other, PP currently has a lower cost and fibers formed from it have a greater tensile strength, while PE currently has a greater cost and fibers formed from it have a lower tensile strength but greater pliability and a more smooth/slippery feel. Accordingly, it may be desirable to form nonwoven web fibers from a blend of PP and PE resins, finding a balance of the best proportions of the polymers to balance their advantages and disadvantages. In some examples, the fibers may be formed of PP/PE blends such as described in U.S. Pat. No. 5,266,392. A suitable spunbond nonwoven may be formed in multiple layers containing differing materials. For example, the spunbond nonwoven may have a standard polypropylene forming the layers on the inner-facing side of the nonwoven, and a polypropylene blend containing softeners for the layers of the outer-facing side of the nonwoven. An exemplary polypropylene blend containing softeners is ExxonMobil SFT-315; however other resins and resin blends designed for use in manufacturing soft nonwovens may also be used.

A nonwoven may be formed from any of these resins by conventional spunbonding processes, in which the resin(s) are heated and forced under pressure through spinnerets. The spinnerets eject fibers of the polymer(s), which are then directed onto a moving belt; as they strike the moving belt they are laid down in somewhat random orientations to form a spunlaid batt. The batt then may be calender-bonded to form the nonwoven web.

Nonwovens formed of any basis weight may be used. However, as noted in the background, relatively higher basis weight, while having relatively greater apparent caliper and loft, also has relatively greater cost. On the other hand, relatively lower basis weight, while having relatively lower cost, adds to the difficulty of providing a backsheet that has and sustains a dramatic visual quilted appearance following compression in a package. It is believed that the combination of features described herein strikes a good balance between controlling material costs and providing a dramatic visual quilted appearance when the basis weight of the nonwoven used is 30 gsm or less, preferably from 20 to 30 gsm, or even more preferably from 23 to 27 gsm.

It is believed that the desired overall visual softness signals of a backsheet laminate may be better achieved when the backsheet laminate is substantially white in color, and has an Opacity of at least 65, more preferably at least 70, even more preferably at least 73, and still more preferably at least 75, as measured by the Opacity Measurement Method set forth below. Accordingly, it may be desirable to add a white-tinting/opacifying agent also to the polymer(s) forming the polymeric film, and to all of the polymer(s) supplying all of the spinnerets.

With respect to a nonwoven web that may form a component of an absorbent article including a topsheet or a backsheet, it was previously believed that adding a white tinting agent to only the polymer(s) forming a first, underlying layer of spunlaid fibers, while adding none to the polymer(s) forming one or more of the overlying spunlaid layers, helped enhance visual softness attributes as a result of the relatively translucent, shiny untinted fibers interacting with ambient light and the white-tinted underlying fibers. However, it has been surprisingly discovered that the desired visual quilted appearance, manifest in a more dramatic visual "popping out" of the impressed pattern, may be more effectively enhanced when substantially all fibers forming the nonwoven are white-tinted/opacified, rather than just one layer, or only some of them. Accordingly, it is believed desirable that a white-tinting/opacifying agent be added to all polymer resin that is spun to make the nonwoven, rather than just that portion of resin that is supplied to a first beam or die leading to a first bank of spinnerets. It is believed that adjusting the opacity of the nonwoven web, through addition of an opacifying agent, may be desirable, such that the nonwoven web has an Opacity of at least 36, more preferably at least 42, and still more preferably at least 45.

While a variety of whitening/opacifying agents may suffice, it is believed that titanium dioxide ($TiO_2$) may be particularly effective because of its brightness and relatively high refractive index. It is believed that addition of $TiO_2$ to the polymer(s) from which the fibers are to be formed, in an amount up to 5.0% by weight of the nonwoven, may be effective to achieve the desired results. However, because $TiO_2$ is a relatively hard, abrasive material, inclusion of $TiO_2$ in amounts greater than 5.0% by weight may have deleterious effects, including wear and/or clogging of spinnerets; interruption and weakening of the structure of the fibers and/or calender bonds therebetween; undesirably increasing the surface friction properties of the fibers (resulting in a less smooth tactile feel); and unacceptably rapid wear of downstream processing equipment components. While 5.0% by weight $TiO_2$ may be an upper limit, if may be more desirable to include no more than 4.0% or even no more than 3.0% by weight $TiO_2$. In order to desirably affect the appearance of the visible outer-facing side of the nonwoven, each layer may include a minimum of 1.5%, to 3%, by weight $TiO_2$, more preferably 1.5% to 2%, and even more preferably, about 1.75%. It is believed that the increased opacity provided by whitener added to the layers of the outer-facing visible side helps to produce the visually distinctive appearance of the nonwoven.

Spunbonding includes the step of calender-bonding the batt of spunlaid fibers, to consolidate them and bond them together to some extent to create a fabric-like structure and enhance mechanical properties e.g., tensile strength, which may be desirable so the material can sufficiently maintain structural integrity and dimensional stability in subsequent manufacturing processes, and in the final product in use. Calender-bonding may be accomplished by passing the batt through the nip between a pair of rotating calender rollers, thereby compressing and consolidating the fibers to form a web. One or both of the rollers may be heated, so as to promote plastic deformation, intermeshing and/or thermal bonding/fusion between superimposed fibers compressed at the nip. The rollers may form operable components of a bonding mechanism in which they are urged together by a controllable amount of force, so as to exert the desired compressing force/pressure at the nip. In some processes heating may be deemed unnecessary, since compression alone may generate sufficient energy within the fibers to effect bonding, resulting from rapid deformation and frictional heat generated in the fibers as they are urged against each other where they are superimposed, resulting in plastic deformation and intermeshing, and possibly thermal bonding/fusion. In some processes an ultrasonic energy source may be included in the bonding mechanism so as to transmit ultrasonic vibration to the fibers, again, to generate heat energy within them and enhance bonding.

One or both of the bonding rollers may have their circumferential surfaces machined, etched, engraved or otherwise formed to have thereon a pattern of protrusions and recessed areas, so that bonding pressure exerted on the batt at the nip is concentrated at the outward surfaces of the protrusions, and reduced or substantially eliminated at the recessed areas. As a result, an impressed pattern of bonds between fibers forming the web, somewhat corresponding to the pattern of protrusions on the roller, is formed on the nonwoven web. One roller may have a smooth, unpatterned cylindrical surface, and the other may be formed with a pattern as described; this combination will impart a pattern on the web somewhat reflecting the pattern on the formed roller. In some examples both rollers may be formed with patterns, and in particular examples, differing patterns that work in combination to impress a combination pattern on the web such as described in, for example, U.S. Pat. No. 5,370,764.

Figure 3A:
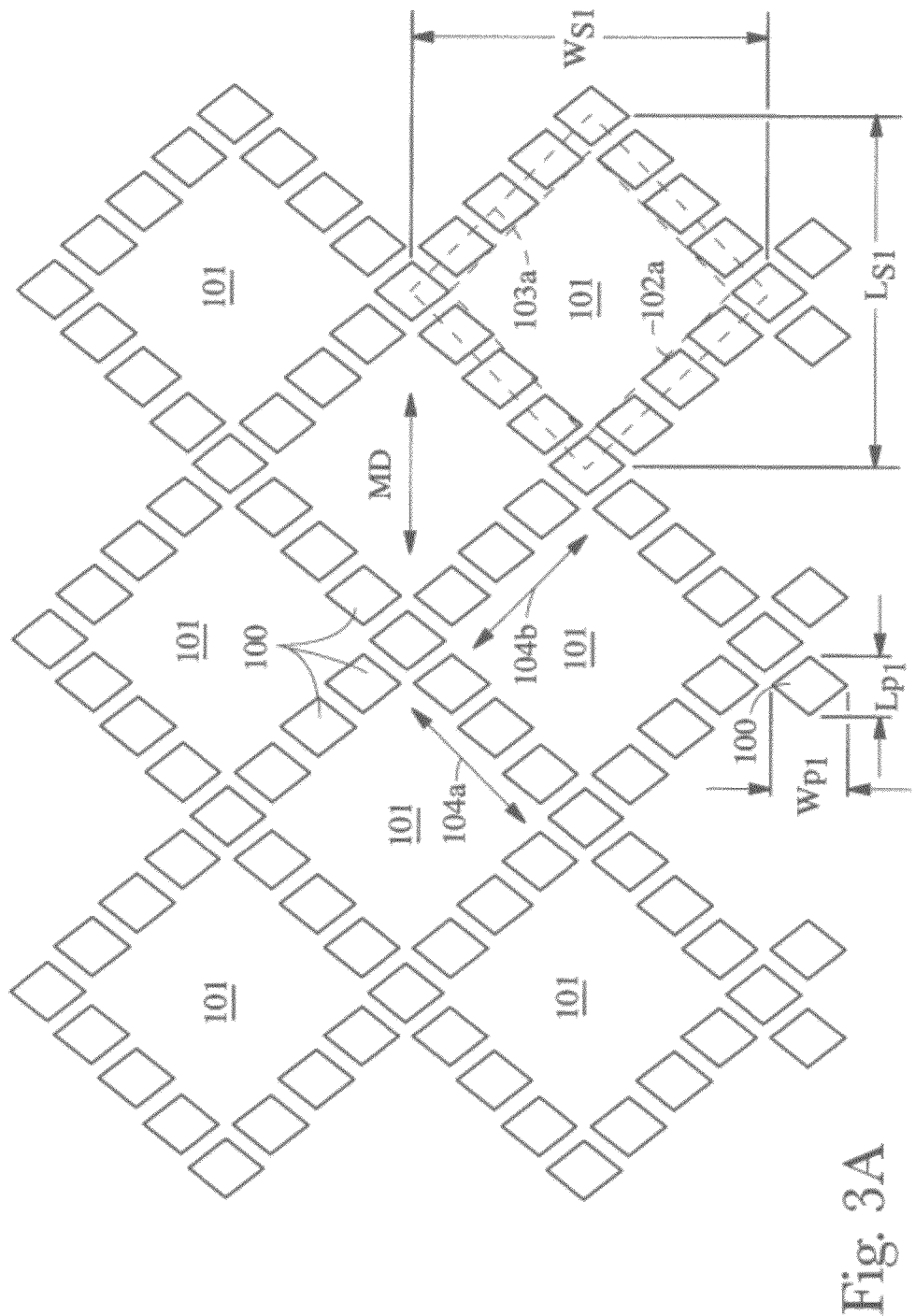
FIG. 3A is a schematic depiction of a pattern(s) that may be machined, etched, engraved or otherwise formed on the working surface of a calender-bonding roller.
Figure 3B:
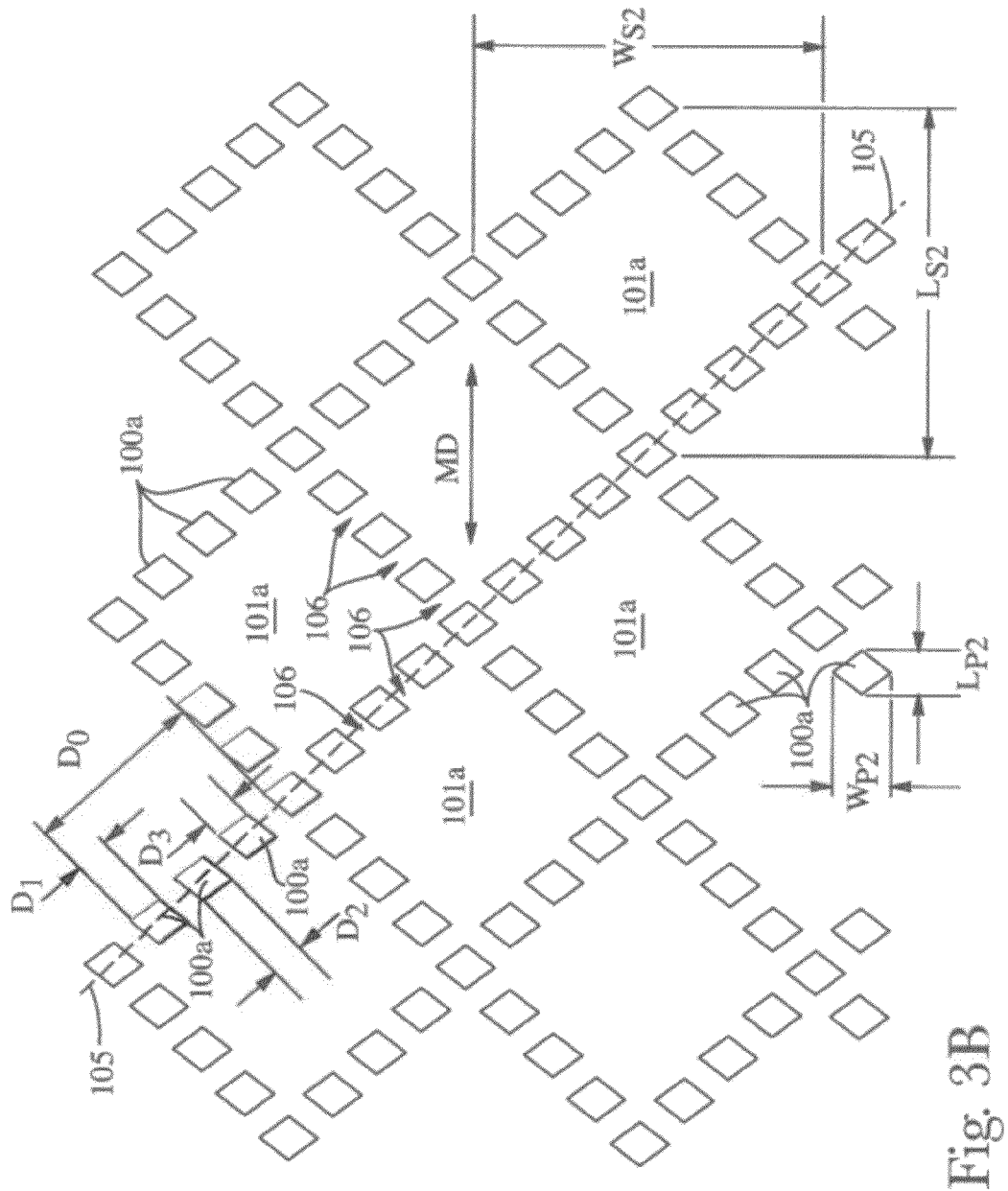
FIG. 3B is a schematic depiction of a pattern(s) of bond impressions that may be impressed on a nonwoven web.

A repeating pattern of protrusions and recessed areas such as, for example, depicted in FIG. 3A, may be formed onto one roller. The smaller shapes depicted in FIG. 3A represent outlines of rhombus- or diamond-shaped raised surfaces 100 of protrusions, while the areas between them represent recessed areas 101. Each protrusion surface may be imparted with a width $W_{P1}$ (relative the machine direction MD) and a length $L_{P1}$, such that each protrusion surface 100 has an area. Without intending to be bound by theory, it is believed that the visual impact of the bond impressions impressed on the web, as well as the tensile strength, resulting from the protrusion surfaces 100, may be affected by the area of the protrusion surfaces 100. Accordingly, it is believed desirable that the average area of the individual protrusion surfaces 100 be from 0.74 mm² to 1.12 mm², or from 0.84 mm² to 1.02 mm², or even from 0.88 mm² to 0.98 mm². Protrusion surfaces 100 may have diamond shapes as shown, or may have any other suitable shape, although it is believed that a diamond, rectangle, square or oval shape may have the desirable effect of simulating the appearance of stitching, as in a quilt.

As can be seen in FIG. 3A, protrusion surfaces 100 may be arranged such that they substantially circumscribe a repeating pattern of recessed areas 101 in the form of geometric shapes. The geometric shapes may be contiguously arranged as depicted. The geometric shapes may be diamonds or squares, as depicted (and illustrated by dotted outlines 102a, 103a in FIG. 3A), or may have other shapes, including but not limited to triangles, diamonds, parallelograms, other polygons, circles, hearts, moons, etc. In FIG. 3A, it can be seen also that the pattern of geometric shapes repeats in the machine and cross directions at frequencies determined by the dimensions of the shape circumscribed by outline 103a, where outline 103a is drawn through the centers of the protrusion surfaces 100. It can be seen that the dimensions of the shape circumscribed by outline 103a correspond with shape length $L_{S1}$ and shape width $W_{S1}$ as shown in FIG. 3A. (Again, length and width are designated with reference to the machine direction MD.) Without intending to be bound by theory, within the ranges of basis weights of spunbond nonwoven materials contemplated herein, it is believed that the size of the repeating geometrically-shaped recessed areas 101 may be impactful with respect to optimizing both the apparent and actual desired visible "pop" of the pattern.

It may be desired that the shapes circumscribed by the bond impressions repeat at a frequency of from 99 to 149, or from 105 to 143, or even from 111 to 137 per meter, in either or both the machine and cross directions, on the nonwoven web. Referring to FIG. 3B, for example, this would means that length $L_{S2}$ and/or width $W_{S2}$ may each be about 6.7 mm to 10.1 mm, or from 7.0 mm to 9.5 mm, or even from 7.3 mm to 9 mm. Alternatively, it may be desired that the repeating shapes defined by the bond impressions (for example, as illustrated/suggested by the repeating square or diamond shape defined by outline 103a, FIG. 3A), have areas from 52 mm² to 78 mm², or from 55 mm² to 75 mm², or even from 58 mm² to 72 mm².

As noted, calender-bonding may be used to consolidate the spunlaid fiber batt into a fabric-like nonwoven web and to impart mechanical strength, e.g., tensile strength, to the web. Generally, within the ranges contemplated herein, greater percentages of protrusion surface area to total patterned roller surface area on a roller formed with a given pattern impart greater tensile strength to the web, than lesser percentages. However, this may come at the cost of added stiffness in the web, which may negatively impact tactile softness attributes. It is believed that a suitable balance between imparting sufficient tensile strength for subsequent processing and satisfactory structural strength in the finished product, and preserving tactile softness attributes, may be struck when the ratio of area of the protrusion surfaces (e.g., protrusion surfaces 100, FIG. 3A) to the total patterned roller surface area is from 16% to 35%, or from 17% to 30%, or even from 18% to 25%.

It will be noted in FIG. 3A that protrusion surfaces 100 appear to form interrupted paths, in the example depicted, along directions indicated by arrows 104a, 104b. Without intending to be bound by theory, it is believed that the interruptions provide at least two beneficial effects. First, it is believed that the resulting bond impressions in the web have the effect of simulating the appearance of stitching, as in a quilt. Second, it is believed that the interruptions in the bond paths provide a multitude of natural hinge points at which the web may flex about the discrete bonds, helping to preserve or enhance pliability in the web despite the presence of the bonds. When a spunlaid batt is passed through a nip formed by a calendering roller having the pattern depicted in FIG. 3A, bonds among and between the fibers are formed beneath protrusion surfaces 100. If these surfaces were continuous along directions 104a, 104b instead of interrupted as shown, the resulting bonds would also be substantially continuous along those directions. This could cause the resulting nonwoven web to be more stiff and less pliable, undesirably comprising its tactile softness attributes.

It will also be noted in FIG. 3A that the directions 104a, 104b followed by the bonding pattern paths may be diagonal with respect to the machine direction. The bond paths imposed on the resulting web will be similarly diagonal with respect to the machine direction. Without intending to be bound by theory, and relative to the use of increased calender-bonding pressure and/or roller temperature to form more fully developed bonds as described herein, it is believed that these paths, when formed of more fully-developed bonds, comprise diagonal paths or linear zones along which the nonwoven web has relatively higher tensile strength and resistance to elongation. It is believed that an interesting effect may result. When these paths are diagonal relative the machine direction and in a criss-crossing pattern as depicted, a net-like structure may be present within the web. As a result, drawing the nonwoven web under tension in the machine direction (as it would be drawn in downstream manufacturing processes, e.g., laminating the nonwoven with a polymer film to form backsheet material) may have the effect of causing the geometric shapes 101 to slightly protrude or "pop" in the z-direction out of the general plane of the web material surface as it narrows in width (exhibiting Poisson effect behavior), or "necks" slightly, as a result of forces within the material under tension in the machine direction, influenced by the net-like structure of diagonal paths of higher tensile strength formed by the bonds.

It is believed that a pattern of diagonally-oriented bonding paths, as suggested in FIGS. 3A and 3B, may be more effective for producing the z-direction "pop" effect described above, than other possible configurations. It is believed, further, that along such diagonally-oriented bonding paths, a greater percentage of bonded material along the paths will have a more dramatic impact than a lesser percentage, because the bonding results in the above-mentioned effect of forming a line along the nonwoven of relatively greater tensile strength and resistance to elongation. Thus, referring to FIG. 3B, it can be seen that a line 105 can be traced a path of bond impressions 100a (line 105 is drawn through the centers of bond impressions 100a, in the depicted example). In order that path 105 exhibits sufficiently greater tensile strength and resistance to elongation than neighboring/parallel lines or paths in the material, it may be desirable that the Bond Length Ratio of a segment along line 105 is between 35% and 99%. However, as noted, it may be desirable not to impart too much stiffness to the web (which compromises a tactile softness attribute). Thus, it may be desirable that the Bond Length Ratio of a bond path be between 35% and 80%, more preferably between 35% and 65%, and even more preferably between 35% and 55%.

It has been learned that more fully-developed bonds and a more highly-defined bond pattern may be more effectively achieved when the protrusion surfaces 100 are polished such that they are relatively smooth, rather than having a rougher, machined surface.

In order to complement the z-direction "pop" effect, in which the material forming unbonded areas 101a protrudes out of the general plane approximated by the web surface, it may be desirable that the pattern of bond impressions 100a (e.g., FIG. 3B) be distinct to the naked eye. In order to achieve this, sufficient force between the calendering rollers should be applied, in combination with sufficient heating temperature. As a result, a visibly distinct pattern of bonds may be achieved, and this pattern will have measurable features. Depending upon bonding pressure and temperature used, the shape and area of the protrusion surfaces 100 will be somewhat reflected in the shape and area of the bond impressions in the nonwoven web. Generally it may be desired that calender bonding pressure and/or roller temperature be adjusted so as to cause the shape and area of protrusion surfaces 100 to be substantially reflected in the shape and area of the bond impressions.

It was previously believed that relatively lighter calender bonding pressures and/or relatively cooler bond roller temperatures were required for calender bonding, to avoid tightly binding down fibers, such that they were no longer available to be fluffed by downstream hydroengorging processes intended to enhance visual and tactile softness attributes. Similarly, while creating more fully developed bonds was thought to be required to improve tensile strength properties, it was believed that creating more fully-developed, rigid bonds through relatively greater calendering pressures and/or roller temperatures would have the effect of undesirably increasing stiffness of the nonwoven, unacceptably compromising its tactile softness attributes. In short, it was believed that to preserve or gain tactile and visual softness signals, it was necessary to compromise tensile strength.

However, it has been discovered, surprisingly, that under the circumstances and conditions described herein, negative effects of greater bonding pressures and/or temperatures upon tactile softness attributes may be insubstantial and/or may be overcome by the positive effects upon visual softness attributes. More particularly, it has been discovered that a more highly-defined bond pattern and quilt "pop" may be enabled through use of relatively increased calender bonding pressures and/or roller temperatures, resulting in more fully-developed bonds, which appears to be effective at creating a product that creates overall visual impressions of softness that may overcome any negative effects upon tactile softness signals resulting from increased stiffness in the material.

Further, it has been discovered, surprisingly, that one tactile softness signal, pliability (sometimes known as "drape"), can be substantially maintained or only insubstantially affected with the nonwoven materials under circumstances contemplated herein, even where more fully developed bonds are created, using bond patterns having features such as those described above. Without intending to be bound by theory, it is believed that interruptions in the bond paths, for example, such as those described above (e.g., interruptions 106, FIG. 3B), may provide natural hinge points at which the material may flex easily about bonds, even in the presence of more fully developed bonds. Although the phenomenon is not thoroughly understood, it is believed that this hinge effect, combined with the multitude of relatively small bond sites separated by unbonded areas such as described and depicted herein (e.g., unbonded areas 101a, FIG. 3A), result in effective substantial preservation of pliability or drape even when the bond sites are more fully developed through relatively increased calender bonding pressures and/or temperatures.

At the same time, creating more fully developed bond sites may add tensile strength in the machine and/or cross directions. Thus, counterintuitively, it has been discovered that tensile strength can be substantially increased through creation of more fully developed calender bonds, without a corresponding, deleteriously substantial negative effect on a tactile softness signal, pliability. This effect may be achievable using features of roller patterns as described herein, with suitably adjusted calender force/pressure and roller temperature, to impress a Bond Area Percentage in the nonwoven web of at least 10%, preferably not more than 20%, more preferably 10% to 17%, and even more preferably 10% to 15%.

Referring to FIGS. 3A and 3B by way of example, it is believed that the size, shape and area of bond impressions 100a in the nonwoven web product will somewhat, but not identically, reflect the size, shape and area of calender roller protrusion surfaces 100. It is believed that the extent to which the area(s) of bond impressions 100a reflect the area(s) of roller protrusion surfaces 100 may be affected by the bonding force/pressure between the calender rollers at the nip, and/or the roller temperature, and generally, that increasing bonding force/pressure and/or roller temperature will increase the area of bond impressions 100a relative the area of protrusion surfaces 100. Thus, if the area of a protrusion surface 100 is from 0.74 mm$^2$ to 1.12 mm$^2$, or from 0.84 mm$^2$ to 1.02 mm$^2$, or even from 0.88 mm$^2$ to 0.098 mm$^2$ as set forth above, it is believed that generally the area of a corresponding bond impression will be somewhat less. In order to achieve the visibly improved results realized in Example 2 herein, bond impressions 100a were created having an average surface area of 0.57±0.06 mm$^2$, resulting from protrusion surfaces 100 having an average surface area of approximately 0.93 mm$^2$. In a prior version, using the same basis weight spunbond batt and the same rollers, the resulting average bond impression surface area was measured as 0.27±0.02 mm$^2$, resulting from a relatively lighter calender pressure and/or roller temperature. It is believed that an increase in calender pressure and/or roller temperature is at least partially the cause for the difference.

Following calender bonding, the web may be subjected to a hydroengorgement process such as described in U.S. Pat. App. Pub. No. 2006/0057921. A distinguishing feature of hydroengorgement, as compared with traditional hydroentanglement, is the use of hydraulic jets to enhance the loft and softness attributes of a nonwoven. However, prior use of hydroengorgement has not been fully satisfactory for providing a nonwoven having both improved softness and a bond pattern with a visually distinct appearance. The '921 application describes a hydroengorgement process involving particular ranges of pressure, e.g., 180-240 bar (2,610-3,480 p.s.i.) applied to the water jet orifices, which was believed required to obtain a desired amount of fluffing of the nonwoven fibers, adding apparent and actual loft or caliper. However, it has been discovered that substantially reducing the hydroengorgement pressure from these magnitudes may still provide desired fluffing without deleterious effects. It is believed that hydroengorgement pressures of the magnitude specified in the '921 application may result in a loss of distinctiveness and/or obscuring of the pattern of bond impressions. Substantially reducing hydroengorgement pressure and energy, and directing hydroengorgement jets at only the inner-facing surface of the nonwoven (thus urging fibers/portions thereof impinged by water jets toward the outer-facing surface) appears to have had a contribution to improving the definition and visual "pop" of the quilt appearance on the outer-facing surface imparted by the roller pattern. A reduced pressure of about 25-100 bars (360-1,450 p.s.i.) may be employed for hydraulic treatment. More preferably, two injectors, each at about 50 bars (725 p.s.i.) of pressure are used, providing an energy transmission of about 0.02 kwhr/kg. It is believed that the use of a one-sided hydroengorgement significantly improves the softness attributes of the nonwoven while pushing fibers in between bond areas to create a more pronounced appearance. Further, the hydroengorgement may enhance the resilience of the pattern such that it can maintain a pronounced appearance after being processed into an article and packaged.

In addition to the features, methods and materials described above, it is believed that the manner in which the nonwoven web is adhered to the polymeric film, to form a backsheet laminate, may have an impact on the quilted appearance of the backsheet. In particular, use of a thermoplastic polymeric hot melt adhesive to adhere the nonwoven web to a thin polymeric film to form a backsheet laminate may enhance the quilted appearance. Without intending to be bound by theory, it is believed that, following lamination, the adhesive contracts slightly as it cools, causing the film, and correspondingly, the laminate, to pucker slightly. This may contribute to causing the unbonded areas of the nonwoven (e.g., unbonded areas 101a, FIG. 3b), to protrude or pop slightly in the z-direction.

If this theory is correct, it may also be desired to apply the hot melt adhesive in a pattern such that adjacent areas and patterns of the nonwoven and polymer film are adhered and not adhered. This allows unadhered areas of the nonwoven to pop in the z-direction away from the film when the laminate is shifted about, such as during handling or wear, contributing to the quilted appearance. Accordingly, in one example, adhesive may be applied in 1 mm wide strips extending along the machine direction, at 3 to 4 strips per centimeter along the cross direction. In another example, adhesive may be applied in a spiral pattern, or series of spiral patterns, leaving unadhered areas surrounded and interspersed with adhered areas.

Further, the polymer film may be stretched slightly in the machine direction prior to, and maintained in the stretched condition during, lamination to the nonwoven web. In this event, subsequent relaxation and elastic contraction of the film following lamination may cause slight machine direction compression of the nonwoven web and thereby promote z-direction protrusion of unbonded areas thereof, potentially enhancing visual "pop" by yet another mechanism. A polymer film may be stretched from 1% to 5% in machine-direction length prior to lamination, or more preferably, from 2% to 4%.

Example 1

An exemplary embodiment of the present invention, Sample A, was a spunbond nonwoven made in a four beam process, laying down four layers (layers A, B, C, D) of fibers, two layers formed of ExxonMobil 3155 polypropylene and two layers formed of ExxonMobil SFT315 polypropylene blend with the bottom layers of the nonwoven being made from ExxonMobil 3155. Each layer contained 2.5% by weight of a master batch containing about 30% by weight polypropylene and 70% $TiO_2$ (a whitener), corresponding to about 1.75% by weight $TiO_2$ for the layer. The spunbond nonwoven was bonded using the bond pattern described for Example 2 below. The bottom side of the nonwoven was hydraulically treated using two rows of jets, each at 50 bars (725 p.s.i.) pressure, for a total energy transmission of 0.02 kwhr/kg.

By comparison, Control A was made from the same nonwoven substrate and bond pattern with only about 0.3% of whitener in each layer. Further, Control A was hydroengorged using a hydraulic treatment on both sides of the nonwoven each side being subjected to a row of jets at a pressure of 240 bars (3,480 p.s.i.).

An additional sample, Control B was made from the same nonwoven with the same processing conditions as Sample A but without any hydraulic treatments.

A third sample, Control C was made with the same nonwoven as Sample A however the whitener distribution was limited to 1.6% on the top layers with no whitener on the bottom layers. The nonwoven was hydroengorged using 2 injectors at 100 bars (1,450 p.s.i.) pressure on the top side, followed by 2 injectors at 250 bars (3,626 p.s.i.) pressure on the bottom side.

In a comparison, Sample A had a significantly improved appearance over Control A, both in raw nonwoven form and when incorporated into an article. Sample A also had an improved appearance over Control B and a significantly improved softness as measured by a panel of testers. In comparison to Sample A, Control C had an inferior visual appearance after manufacture and showed significant deterioration in appearance after being incorporated into an article and packaged. Table 1 sets forth properties of Control A, Control B, Control C and Sample A.

TABLE 1

| Description | Control A | Control B | Control C | Sample A |
|---|---|---|---|---|
| Process Conditions | | | | |
| Whitener Distribution (layers A-D), weight % | 0.3 × 4 | 2.5 × 4 | 1.6, 1.6, 0, 0 | 2.5 × 4 |
| Spinbelt speed, meters/m | 420 | 440 | 420 | 440 |
| HE Injector Pressures, C1, C2, bar | 1 × 240, 1 × 240 | 2 × 0, 2 × 0 | 2 × 100, 2 × 250 | 2 × 0, 2 × 50 |
| HE Energy, kwhr/kg | 0.20 | 0.00 | 0.26 | 0.02 |
| Physical Properties | | | | |
| Basis Weight, gsm | 26.1 | 24.7 | 24.9 | 24.1 |
| MD Tensile Strength, gf/cm | 795 | 918 | 673 | 938 |
| MD Elongation, % | 39.5 | 55.7 | 36.9 | 43.1 |
| CD Tensile Strength, N/cm | 489 | 449 | 347 | 489 |
| CD Elongation, % | 58.6 | 63.0 | 59.3 | 65.7 |
| MD:CD | 1.62 | 2.05 | 1.95 | 1.92 |
| Air Perm, m$^3$/m$^2$/min | 170 | 163 | 192 | 171 |
| Caliper, mm | — | 0.275 | 0.271 | 0.296 |
| Opacity, % | 33.2 | 47.8 | 33.6 | 45.7 |
| Hand Panel Survey | Not Tested | 0 | Not Tested | 10 |
| Quilt Definition of Nonwoven | Poor | Very Good | Good | Excellent |
| Quilt Definition after Packaging | Poor | | Fair | Excellent |

Example 2

An improved backsheet laminate including an improved spunbond nonwoven web laminated/adhered to a polymeric film was manufactured. The nonwoven web was calender-bonded in a pattern, between the nip between a pattern calender roller and a smooth calender roller as described herein, to impart a pattern of bond impressions as schematically suggested in FIG. 3B. The improved web had a basis weight of about 25 gsm and comprised PP.

The web was manufactured by First Quality Nonwovens, Inc., Great Neck, N.Y., using a calender roller bearing a repeating "P11" pattern as schematically depicted in FIG. 3A, as provided by The Procter & Gamble Company, Cincinnati, Ohio, and manufactured by Ungricht Roller & Engraving Technology (A.+E. Ungricht GmbH+Co KG), Monchengladbach, Germany. Referring to FIG. 3A, the engraving/machining specifications for the roller pattern were such that $W_{S1}$ and $L_{S1}$ were each 8.077 mm; $W_{P1}$ was 1.69 mm; and $L_{P1}$ was 1.1 mm, such that the protrusion surface 100 areas were each 0.93 mm$^2$.

The improved laminate had a dramatically improved, visually distinct quilted appearance and exhibited a dramatically improved visible pattern of light and shadow under varying lighting conditions, as compared with prior versions. The bond impressions were more visible to the naked eye, and more clearly defined. The Total Bond Area was estimated from the measured Average Individual Bond Area and the roller pattern repeat dimensions (8.077 mm each way) as approximately 12% to 13%.

Various features of the resulting improved nonwoven web and laminate were measured and compared with those of prior versions of nonwoven webs and laminates formed therewith, and having similar calender bonding patterns. It is believed the improved quilted appearance resulted from a combination of one or more of increased Opacity, increased Average Measured Height, increased Average Individual Bond Area and/or other features. As can be seen in Table 2, the improved nonwoven web also had improved tensile strength in both machine and cross directions over the prior versions, except for machine direction tensile strength compared with prior version C; but version C had approximately 52% greater basis weight.

TABLE 2

| Sample | Basis Weight (gsm)/construction | Nonwoven Web MD Tensile Strength (gf/cm) | Nonwoven Web CD Tensile Strength (gf/cm) | Opacity of Laminate | Opacity of Nonwoven Web | Nonwoven Total Stiffness (g/f) | Nonwoven Average Measured Height (μm) | Average Individual Bond Area (mm$^2$) |
|---|---|---|---|---|---|---|---|---|
| Improved | ~25/spunlaid | 970 | 441 | 76 | 52 | 8.7 | 318 | 0.57 |
| Prior Version A | ~25/spunlaid | 679 | 298 | 72 | 34 | 7.4 | 170 | 0.27 |
| Prior Version B | ~25/spunlaid bicomponent fiber | 822 | 266 | 68 | 32 | 6.6 | 274 | 0.27 |
| Prior Version C | ~38/carded | 1,051 | 181 | 70 | 39 | 13.9 | 354 | 0.54 |

In-Bag Compression Measurement Test

I. Determine Free Stack Height
  Equipment
    Universal Diaper Packaging Tester (UDPT), including a vertical sliding plate for adding weights. It is counterbalanced by a suspended weight to assure that no downward force is added from the vertical sliding plate assembly to the diaper package at all times. The UDPT is available from Matsushita Industry Co. LTD, 7-21-

101, Midorigaoka-cho, Ashiya-city, Hyogo JAPAN. Zip code: 659-0014. For further details concerning this Tester, see U.S. Pat. App. Pub. No. 2008/0312624.

A 850 g (±5 g) weight.

Stopwatch with an accuracy to 1 second.

Test Procedure

A) Apparatus Calibration

Pull down the vertical sliding plate until its bottom touches the tester base plate.

Set the digital meter located at the side of the vertical sliding scale to zero mark.

Raise the vertical sliding plate away from the tester base plate.

B) Definitions

Before-bagger free height refers to the free height data measured on 10 pads of fresh diapers.

Fresh Diapers—10 diapers that have never been compressed (stack should be removed (where safely possible) immediately after exit from stacker, before any compression has occurred. If this is not possible, they should be removed from the fingers of a safely stopped stacker chain).

Out-bag free height designates the free height data measured on 10 pads of aged diapers.

Aged Diapers—10 diapers that have been held under compression for approximately 1 minute and/or longer (i.e. 10 diapers come from a freshly opened diaper package).

C) Free Height Measurement

Select 10 adjacent pads of diapers out of the middle from an appropriate source; Fresh diapers for before-bagger free height; Aged diapers for out-of-bag free height.

Neatly stack these 10 pads of diapers underneath the vertical sliding plate. (Align the center of the top pad directly below the central counter sunk hole of the vertical sliding plate.)

Place the 850 g weight onto the vertical sliding plate.

Allow the vertical sliding plate to slide down until its bottom lightly touches desired highest point of the stack.

Measure the stack dimensions in mm by reading the value that appears on the digital meter.

Remove the weight.

Raise the vertical sliding plate away from the stack and remove the stack.

Record the stack height reading to the nearest 1 mm shown on the digital meter.

Procedure—Aging Profile

A) Collect a minimum of three data points from different sample sets e.g., Measure first point from fresh diapers, e.g., measure second point from diapers being aged in bag for 30 mm/1 hr/6 hr/12 hr/24 hr, e.g., measure third point from diapers being aged in bag for 5 days or longer.

B) Repeat the three steps as described in "Test Procedure" steps A), C), and D).

Procedure—Out-of-Bag Free Height Recovery

A) Collect 10 pads of fresh/aged diapers.

B) Repeat the first two steps as described in "Test Procedure" steps A) and C).

C) Repeat the steps above for general free height measurement except changing the waiting time (i.e., measure first point at 1 min and remaining points at 30 mm/1 hr/6 hr/12 hr/1 day/3 days/5 days, or longer).

Calculation/Reporting

Report Sample Identification, i.e. complete description of product being tested (product brand name/size).

Report the determined value for all measurement to the nearest 1 mm.

NOTE: In case of a series of measurements report the number of tested samples, and calculate/report the Average, Standard deviation, Minimum and Maximum of the values.

Report the Production Date of the measured package (taken from package coding).

Report the Testing Date and Analytical Method used (GCAS).

II. Determine In-Bag Stack

Equipment

Universal Diaper Packaging Tester (UDPT), including a vertical sliding plate for adding weights. It is counterbalanced by a suspended weight to assure that no downward force is added from the vertical sliding plate assembly to the diaper package at all times. The UDPT is available from Matsushita Industry Co. LTD, 7-21-101, Midorigaoka-cho, Ashiya-city, Hyogo JAPAN. Zip code: 659-0014.

A 850 g (±5 g) weight.

Definitions

"Package Width" is defined as the maximum distance between the two highest bulging points along the same compression stack axis of a diaper package.

$$\text{In-Bag Stack Height} = (\text{Package Width} / \text{Pad Count Per Stack}) \times 10 \text{ pads of diapers.}$$

Apparatus Calibration

Pull down the vertical sliding plate until its bottom touches the tester base plate.

Set the digital meter located at the side of the vertical sliding scale to zero mark.

Raise the vertical sliding plate away from the tester base plate.

Test Procedure

Put one of the side panel of the diaper package along its width standing at the center of the tester base plate. Make sure the horizontal sliding plate is pulled to the right so it does not touch the package being tested.

Add the 850 g weight onto the vertical sliding plate.

Allow the vertical sliding plate to slide down until its bottom lightly touches desired highest point of the package.

Measure the package width in mm (distance from the top of the base plate to the top of the diaper package). Record the reading that appears on the digital meter.

Remove the 850 g weight.

Raise the vertical sliding plate away from the diaper package.

Remove the diaper package.

Calculation/Reporting $$\text{Calculate and report the "In-Bag Stack Height"} = (\text{Package Width} / \text{Pad Count Per Stack}) \times 10.$$

Report Sample Identification, i.e. complete description of product being tested (product brand name/size).

Report the determined value for each measurement (Length/Width/Front-to-Back) to the nearest 1 mm.

NOTE: In case of a series of measurements report the number of tested samples, and calculate/report the Average, Standard deviation, Minimum and Maximum of the values.

Report the Production Date of the measured package (taken from package coding).

Report the Testing Date and Analytical Method used (GCAS).

III. Calculate %

$$\text{Calculate \%: } 1 - (\text{In-Bag Stack Height})/(\text{Free Stack Height}) = \%$$

Opacity Measurement Method

The opacity of a material is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, Va.). Instrument calibration and measurements are made using the standard white and black calibration plates provided by the vendor. All testing is performed in a room maintained at about 23±2° C. and about 50±2% relative humidity.

Configure the spectrophotometer for the XYZ color scale, D65 illuminant, 10° standard observer, with UV filter set to nominal. Standardize the instrument according to the manufacturer's procedures using the 1.20 inch port size and 1.00 inch area view. After calibration, set the software to the Y opacity procedure.

To obtain the specimen, lay the sample flat on a bench, body facing surface downward, and measure the total longitudinal length of the article. Note a site 33% of the total length from the front waist of the article along the longitudinal axis and a second site, 33% of the total length from the back waist of the article. Carefully remove the backsheet laminate, consisting of both the film and nonwoven web, from the garment-facing side of the article. A cryogenic spray, such as Cyto-Freeze (obtained from Control Company, Houston, Tex.), may be used to separate the backsheet laminate from the article. Cut a piece 50.8 mm by 50.8 mm centered at each site identified above. Precondition samples at about 23° C.±2 C° and about 50%±2% relative humidity for 2 hours prior to testing.

Place the specimen over the measurement port. The specimen should completely cover the port with the surface corresponding to the garment-facing surface of the article directed toward the port. Cover the specimen with the white standard plate. Take a reading, then remove the white tile and replace it with black standard tile without moving the specimen. Obtain a second reading, and calculate the opacity as follows:

$$\text{Opacity} = Y\text{value}_{(black\ backing)} / Y\text{value}_{(white\ backing)} \times 100$$

A total of five identical articles are analyzed and their opacity results recorded. Calculate and report the average opacity and standard deviation for the 10 backsheet laminate measurements to the nearest 0.01%.

Using the same specimens as above, remove the nonwoven web from the film layer for anlysis. The cryogenic spray can once again be employed. Precondition samples at about 23° C.±2 C° and about 50%±2% relative humidity for 2 hours prior to testing. In like fashion, analyze the nonwoven web layer following the above procedure. Calculate and report the average opacity and standard deviation for the 10 nonwoven web measurements to the nearest 0.01%.

Average Measured Height Method

Average Measured Height is measured using a GFM Primos Optical Profiler instrument commercially available from GFMesstechnik GmbH, Teltow/Berlin, Germany. The GFM Primos Optical Profiler instrument includes a compact optical measuring sensor based on digital micro-mirror projection, consisting of the following main components: a) DMD projector with 1024×768 direct digital controlled micro-mirrors; b) CCD camera with high resolution (1300×1000 pixels); c) projection optics adapted to a measuring area of at least 27×22 mm; d) recording optics adapted to a measuring area of at least 27×22 mm; e) a table tripod based on a small hard stone plate; f) a cold light source (an appropriate unit is the KL 1500 LCD, Schott North America, Inc., Southbridge, Mass.); g) a measuring, control, and evaluation computer running ODSCAD 4.14-1.8 software; and h) calibration plates for lateral (x-y) and vertical (z) calibration available from the vendor.

The GFM Primos Optical Profiler system measures the surface height of a sample using the digital micro-mirror pattern fringe projection technique. The result of the analysis is a map of surface height (z axis) versus displacement in the x-y plane. The system has a field of view of 27×22 mm with a resolution of 21 microns. The height resolution should be set to between 0.10 and 1.00 micron. The height range is 64,000 times the resolution. All testing is performed in a conditioned room maintained at about 23±2° C. and about 50±2% relative humidity.

To obtain the specimen, lay the sample flat on a bench, body facing surface downward, and measure the total longitudinal length of the article. Note a site 33% of the total length from the front waist of the article along the longitudinal axis and a second site, 33% of the total length from the back waist of the article. Carefully remove the nonwoven outer cover from the garment-facing side of the article. A cryogenic spray, such as Cyto-Freeze (obtained from Control Company, Houston, Tex.), may be used to separate the nonwoven from the underlying film layer. Cut a piece 40 mm by 40 mm centered at each site identified above. Precondition samples at about 23° C.±2 C° and about 50%±2% relative humidity for 2 hours prior to testing.

Turn on the cold light source. Select settings on the cold light source to give a reading of 3000K on the display (typically 4 and E). Open the ODSCAD 4.14-1.8 Software and select "Start Measurement" and then "Live Pic". Calibrate the instrument according to manufacturer's specifications using the calibration plates for lateral (x-y) and vertical (z) available from the vendor.

Place the 40 mm by 40 mm specimen of nonwoven outer cover, clothing surface upward, under the projection head and on top of a neutral gray surface (WhiBal White Balance Reference, PictureFlow LLC, Melbourne, Fla.). Ensure that the sample is lying flat, without being stretched. This may be accomplished by taping the perimeter of the sample to the surface or placing it under a weighted frame with an inside dimension of 30 mm×30 mm.

Using the "Pattern" command, project the focusing pattern on the surface of the specimen. Position the projection head to be normal to the sample surface. Align the projected cross hair with the cross hair displayed in the software. Focus the image using the projector head height adjustment knob. Adjust image brightness according to the instrument manufacturer's instruction by setting the "Projection" value to 10, and then changing the aperture on the lens through the hole in the side of the projector head. Optimum illumination is achieved when the lighting display indicator in the software changes from red to green. Due to variations in instrument configurations, different brightness parameters may be available. Always follow the instrument manufacturer's recommended procedures for proper illumination optimization.

Select the Technical Surface/Standard measurement type. Operating parameters are as follows: Utilization of fast picture recording with a 3 frame delay. A two level Phasecode, with the first level being defined as an 8 pixel strip width with a picture count number of 24, and the second level being defined as a 32 pixel strip width with a picture count number of 6. A full Graycode starting with pixel 1 and ending with pixel 1024. A Prefiltering routine including the removal of invalid pixels, a 5 by 5 median filter, and a 3 by 3 average filter.

Select "Measure" to capture and digitalize the image. The specimen must remain still during this procedure to avoid blurring of the captured image. The image will be captured in approximately 20 seconds. Save the height image and camera image files.

Figure 4A:
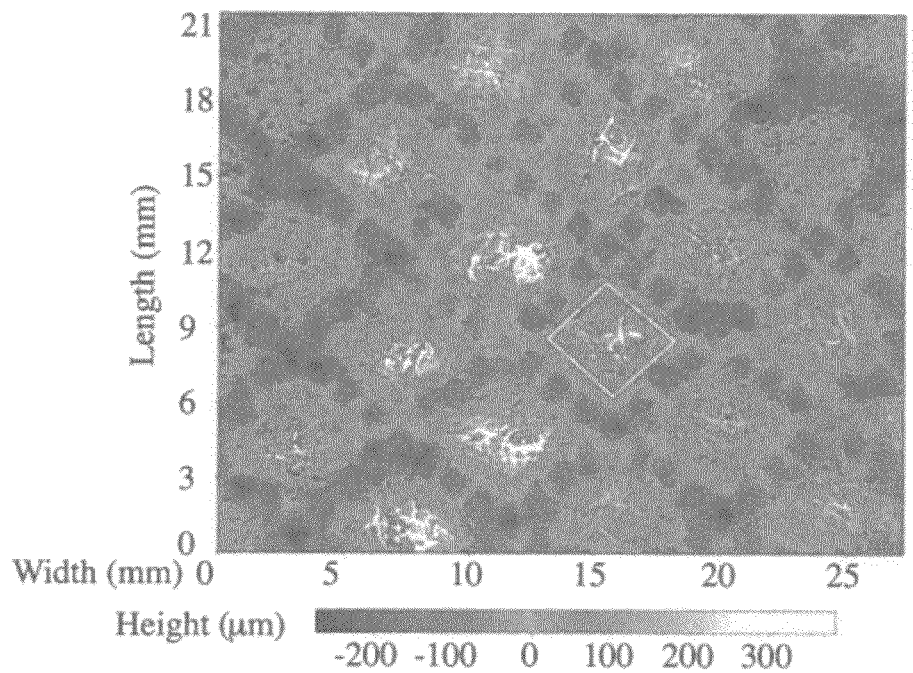
FIG. 4A is an image of a nonwoven web sample taken using equipment described in the Average Measured Height Method set forth herein, illustrating an outline of an unbonded area.
Figure 4B:
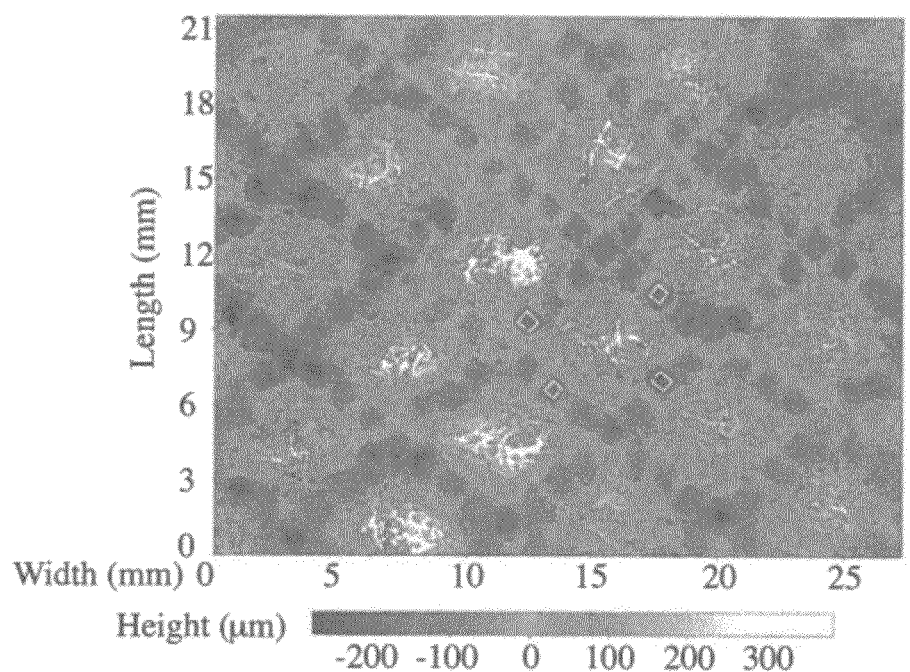
FIG. 4B is an image of a nonwoven web sample taken using equipment described in the Average Measured Height Method set forth herein, illustrating outlines of individual bond impressions.

Load the height image into the analysis portion of the software via the clipboard. Zoom in on a region of interest (ROI) encompassing a single repeating pattern of bond impressions and unbonded area. Using the polygon drawing tool manually outline four individual bond impressions around the perimeter of the unbonded area (see example in FIG. 4B). From "View" select "Histogram of height picture". Select the number of classes as 200 and calculate the frequency histogram. Save the bond impression height file. Returning to the height image, cancel the polygon markings drawn on the bond impressions. Next, using the polygon drawing tool, manually outline the unbonded area surrounded by the bond impressions (see example in FIG. 4A). Once again, from "View" select "Histogram of height picture". Select the number of classes as 200 and calculate the frequency histogram. Save the unbonded area histogram file.

Open the histogram file of the bond impressions, determine the height range value at, or nearest to 50%. Record bond impression height to the nearest 1 micrometer. Open the histogram file of the unbonded area, determine the height range value at, or nearest to 90%. Record the unbonded area height to the nearest 1 micrometer. Measured Height is calculated as follows:

$$\text{Measured Height} = \text{unbonded area height} - \text{bond impression height}$$

Measured Height is measured at two separate ROI's for each of the specimens (i.e., from front of article and back of article) to give four measures per test article. A total of three test articles are analyzed in like fashion. Calculate the Average and standard deviation for all twelve measured Measured Heights and report to the nearest 1 micrometer.

Tensile Strength Measurement Method

Tensile Strength is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips, wider than the width of the test specimen. All testing is performed in a conditioned room maintained at about 23° C.±2 C and about 50%±2% relative humidity.

To obtain the specimen for CD tensile, lay the sample flat on a bench, body facing surface downward, and measure the total longitudinal length of the article. Note a site 25% of the total length from the front waist of the article along the longitudinal axis and a second site, 25% of the total length from the back waist of the article. Carefully remove the nonwoven outer cover from the garment-facing side of the article. A cryogenic spray, such as Cyto-Freeze (obtained from Control Company, Houston, Tex.), may be used to separate the nonwoven outer cover from the underlying film layer. Cut a specimen, with a die or razor knife, which is 50.8 mm wide along the longitudinal axis of the sheet and least 101.6 mm long along the lateral axis of the sheet, centered at each of the sites identified above.

In like fashion prepare MD tensile specimens from a second set of identical samples. Here, after removing the nonwoven outer cover, cut a specimen, with a die or razor knife, which is at least 101.6 mm wide along the longitudinal axis of the sheet and 50.8 mm long along the lateral axis of the sheet, centered at each of the sites identified above. Precondition both CD and MD specimens at about 23° C.±2 C° and about 50%±2% relative humidity for 2 hours prior to testing.

For analyses, set the gage length to 50.8 mm. Zero the crosshead and load cell. Insert the specimen into the upper grips, aligning it vertically within the upper and lower jaws and close the upper grips. Insert the specimen into the lower grips and close. The specimen should be under enough tension to eliminate any slack, but less than 0.05 N of force on the load cell.

Program the tensile tester to perform an extension test, collecting force and extension data at an acquisition rate of 50 Hz as the crosshead raises at a rate of 100 mm/min until the specimen breaks. Start the tensile tester and data collection. Program the software to record Peak Force (gf) from the constructed force (gf) verses extension (mm) curve. Calculate tensile strength as:

$$\text{Tensile Strength} = \text{Peak Force (gf)}/\text{width of specimen (cm)}$$

Analyze all CD tensile specimens. Record Tensile Strength to the nearest 1 gf/cm. Analyses are performed on specimens from the two sites on the article. A total of five test articles are analyzed in like fashion. Calculate and report the average and standard deviation of Tensile Strength to the nearest 1 gf/cm for all ten measured CD specimens.

Next run all MD tensile Specimens. Record Tensile Strength to the nearest 1 gf/cm. Analyses are performed on specimens from the two sites on the article. A total of five test articles are analyzed in like fashion. Calculate and report the average and standard deviation of Tensile Strength to the nearest 1 gf/cm for all ten measured MD specimens.

Image Analysis of Bond Impressions

Area and distance measurements are performed on images generated using a flat bed scanner capable of scanning at a resolution of at least 4800 dpi in reflectance mode (a suitable scanner is the Epson Perfection V750 Pro, Epson, USA). Analyses are performed using ImageJ software (Vs. 1.43u, National Institutes of Health, USA) and calibrated against a ruler certified by NIST.

To obtain the specimen, lay the sample flat on a bench, body facing surface downward, and measure the total longitudinal length of the article. Note a site 33% of the total length from the front waist of the article along the longitudinal axis and a second site, 33% of the total length from the back waist of the article. Carefully remove the nonwoven outer cover from the garment-facing side of the article. A cryogenic spray, such as Cyto-Freeze (obtained from Control Company, Houston, Tex.), may be used to separate the nonwoven from the underlying film layer. Cut a piece 80 mm by 80 mm centered at each site identified above. Precondition samples at about 23° C.±2 C° and about 50%±2% relative humidity for 2 hours prior to testing.

Place the specimen on the flat bed scanner, body side surface facing upward, with the ruler directly adjacent. Placement is such that the dimension corresponding to the MD of the nonwoven is parallel to the ruler. A black backing is placed over the specimen and the lid to the scanner is closed. Acquire an image composed of the nonwoven and ruler at 4800 dpi in reflectance mode in 8 bit grayscale and save the file. Open the image file in ImageJ and perform a linear calibration using the imaged ruler. Reference will be made to FIG. 3B as an example of a repeating pattern of bond impressions. These measures are equally applicable to other bond shapes and repeating bond patterns.

Average Individual Bond Area

Enlarge a ROI such that edges of the bond impression can be clearly determined. With the area tool, manually trace the perimeter of a bond. Calculate and record the area to the nearest 0.001 mm$^2$. Repeat for a total of ten non-adjacent bonds randomly selected across the total specimen. Measurements are made on both specimens from each article. A total of three identical articles are measured for each sample set. Calculate the average and standard deviation of all 60 bond area measurements and report to the nearest 0.001 mm$^2$.

Bond Path/Bond Length Ratio

Identify a single, complete repeating series of bond impressions forming a path and enlarge the image such that the repeating series fills the field of view. Draw a line along the path that connects and extends through all bond impressions in the series (e.g., FIG. 3B, line 105). Measure the dimensions along the line that are included within the bond impressions (e.g. in FIG. 3B, $D_1$, $D_2$, $D_3$). Next, measure the distance of the line segment from the leading edge of the first bond impression in the repeating series to leading edge of the first bond impression in the next adjacent series along the line segment (e.g. in FIG. 3B, $D_o$). Calculate the sum of the lengths of the bonds along the line segment (e.g. $D_1+D_2+D_3$), divided by the length of the line segment, (e.g. $D_o$), ×100%. Record the Bond Path/Bond Length Ratio to the nearest 0.001. Repeat for a total of five non-adjacent ROI's randomly selected across the total specimen. Measurements are made on both specimens from each article. A total of three identical articles are measured for each sample set. Calculate the average and standard deviation of all 60 bond Path/Length Ratio measurements and report to the nearest 0.001 units. Note for irregularly-shaped bond impressions forming a repeating series, locate a line so as to find the maximum sum of the lengths of the bond impressions measurable therealong.

Bond Area Percentage

Identify a single repeat pattern of bond impressions and unbonded areas and enlarge the image such that the repeat pattern fills the field of view. In ImageJ draw a box that encompasses the repeat pattern. For the example shown in FIG. 3B, this would be a box, $W_{S2}$ wide and $L_{S2}$ long. Note, in the example shown in FIG. 3B, the shared bond impressions at the corners are divided in half along the longitudinal or lateral direction as appropriate. Calculate area of the box and record to the nearest 0.01 mm$^2$. Next, with the area tool, trace the individual bond impressions or portions thereof entirely within the box and calculate the areas of all bond impressions or portions thereof that are within the box. Record to the nearest 0.01 mm$^2$. Calculate as follows:

Percent Bond Area=(Sum of areas of bond impressions within box)/(area of box)×100%

Repeat for a total of five non-adjacent ROI's randomly selected across the total specimen. Record as Percent Bond Area to the nearest 0.01%. Measurements are made on both specimens from each article. A total of three identical articles are measured for each sample set. Calculate the average and standard deviation of all 30 of the percent bond area measurements and report to the nearest 0.001 units.

Stiffness

Stiffness of the nonwoven outer cover was measured in accordance with ASTM D6828-02. For analysis a 76.2 mm by 76.2 mm square specimen was used instead of the 100 mm by 100 mm specimen recited in the standard.

To obtain the specimen, lay the sample flat on a bench, body facing surface downward, and measure the total longitudinal length of the article. Note a site 25% of the total length from the front waist of the article along the longitudinal axis and a second site, 25% of the total length from the back waist of the article. Carefully remove the nonwoven outer cover from the garment-facing side of the article. A cryogenic spray, such as Cyto-Freeze (obtained from Control Company, Houston, Tex.), may be used to separate the nonwoven from the underlying film layer. Cut a piece 76.2 mm by 76.2 mm centered at each site identified above. Precondition samples at about 23° C.±2 C° and about 50%±2% relative humidity for 2 hours prior to testing.

Stiffness measurements are made on both specimens from each article. A total of three identical articles are measured for each sample set. Calculate the average and standard deviation of the six Total Stiffness results and report to 0.01 g.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article adapted to be worn about a wearer's lower torso, having a longitudinal axis, and comprising:
  a liquid permeable topsheet;
  a liquid impermeable backsheet; and
  an absorbent core disposed between the topsheet and the backsheet;
  wherein the liquid impermeable backsheet comprises a laminate of:
    a wearer-facing layer of liquid impermeable, vapor permeable polymeric film and a garment—facing layer of nonwoven web, the nonwoven web being impressed with a first pattern of bond impressions, the first pattern of bond impressions defining a second pattern of unbonded pillow regions, wherein the nonwoven web has undergone a hydroengorgement process following a calender bonding process; and
    wherein the nonwoven web:
      is formed of spunlaid fibers comprising polyolefin and up to 3.0% by weight $TiO_2$;
      has a basis weight of 30 gsm or less;
      has an Opacity of 45 or greater; and
      has a Bond Area Percentage of at least 10%; and
  wherein the nonwoven web is bonded to the polymeric film by a thermoplastic polymeric adhesive disposed between the nonwoven web and the polymeric film.

2. The article of claim 1 wherein the spunlaid fibers comprise polypropylene.

3. The article of claim 2 wherein the spunlaid fibers comprise at least 50% by weight polypropylene.

4. The article of claim 1 wherein substantially all of the spunlaid fibers are Monocomponent.

5. The article of claim 1 wherein the nonwoven web has a Tensile Strength in the machine direction of at least 900 gf/cm.

6. The article of claim 1 wherein the nonwoven web has a Tensile Strength in the cross direction of at least 300 gf/cm.

7. The article of claim 1 wherein the nonwoven web has a Total Stiffness of no more than 9.0 gf.

8. The article of claim 1 wherein the first pattern of bond impressions comprises at least two adjacent, parallel, straight paths defined by the bond impressions, wherein a line exists along each path, along which there are bonded lengths separated by unbonded lengths, and the ratio of total bonded length to total unbonded length (Bond Length Ratio) is at least 35% but less than 100%.

9. The article of claim 8 wherein the ratio of bonded distances to unbonded distances is less than 75%.

10. The article of claim 8 wherein the ratio of bonded distances to unbonded distances is less than 60%.

11. The article of claim 8 wherein the bond impressions forming the paths are substantially uniform in shape, and substantially uniformly distributed along the paths.

12. The article of claim 1 wherein the bond impressions have a substantially parallelogram shape.

13. The article of claim 1 wherein the thermoplastic adhesive is applied in strips situated longitudinally along the machine direction, and wherein the laminate has regions having no adhesive, between the strips.

14. The article of claim 13 wherein the longitudinal strips are applied at a frequency of 3 to 4 strips per centimeter along the cross direction.

15. The article of claim 1 wherein the Bond Area Percentage is not more than 20%.

16. The article of claim 1 wherein the polymeric film has been stretched from 1% to 5% along a machine direction prior to being laminated with the nonwoven web.

17. The article of claim 1 wherein the Average Measured height is at least 200 μm.

* * * * *